(12) United States Patent
Rush et al.

(10) Patent No.: US 7,875,243 B2
(45) Date of Patent: Jan. 25, 2011

(54) SENSOR-DISPENSING INSTRUMENTS

(75) Inventors: Benjamin Rush, Evanston, IL (US); Shu Kun Chang, Evanston, IL (US); Jeffery S. Reynolds, Granger, IN (US); Sean Gallimore, Granger, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 814 days.

(21) Appl. No.: 11/792,356

(22) PCT Filed: Dec. 12, 2005

(86) PCT No.: PCT/US2005/044949

§ 371 (c)(1),
(2), (4) Date: Jun. 5, 2007

(87) PCT Pub. No.: WO2006/065754

PCT Pub. Date: Jun. 22, 2006

(65) Prior Publication Data

US 2008/0190766 A1 Aug. 14, 2008

Related U.S. Application Data

(60) Provisional application No. 60/635,667, filed on Dec. 13, 2004.

(51) Int. Cl.
*G01N 15/06* (2006.01)
(52) U.S. Cl. .................................. 422/68.1
(58) Field of Classification Search ............ 422/68.1
See application file for complete search history.

(56) References Cited

U.S. PATENT DOCUMENTS 5,279,294 A 1/1994 Anderson et al. ......... 128/633
5,971,941 A * 10/1999 Simons et al. ............. 600/573
2004/0007585 A1 * 1/2004 Griffith et al. ............. 221/232

FOREIGN PATENT DOCUMENTS

WO    WO 88/00812 A    2/1988

(Continued)

OTHER PUBLICATIONS

Provisional U.S. Appl. No. 60/313,059. Date: Apr. 16, 2010.*

(Continued)

*Primary Examiner*—Walter D Griffin
*Assistant Examiner*—Bobby Ramdhanie
(74) *Attorney, Agent, or Firm*—Nixon Peabody LLP

(57) ABSTRACT

A sensor-dispensing instrument is adapted to determine an analyte concentration of a fluid and comprises a body, a cap, a cartridge, a test-sensor receptacle, and a sensor-advancement mechanism. The cap is adapted to move between an open position and a closed position. The cap and body are adapted to correspond with each other to form the closed position. The cartridge contains a plurality of test sensors. The cartridge is located substantially within the cap. The sensor-advancement mechanism is adapted to advance the plurality of test sensors, one at a time, to a position that allows a user to manually remove the test sensor and place the test sensor in the test-sensor receptacle. The sensor-dispensing instrument may also include a lancing device including a lancet.

35 Claims, 12 Drawing Sheets

FOREIGN PATENT DOCUMENTS

WO          WO 03/082091 A2    10/2003

OTHER PUBLICATIONS

Written Opinion of the International Searching Authority corresponding to co-pending International Patent Application No. PCT/US2005/044949, European Patent Office, dated May 9, 2006, 6 pages.

International Search Report corresponding to co-pending International Patent Application No. PCT/US2005/044949, European Patent Office, dated May 9, 2006, 5 pages.

* cited by examiner

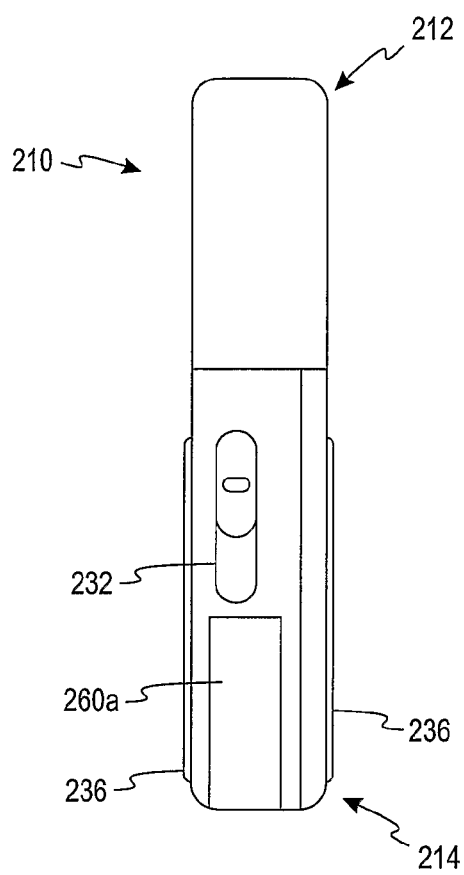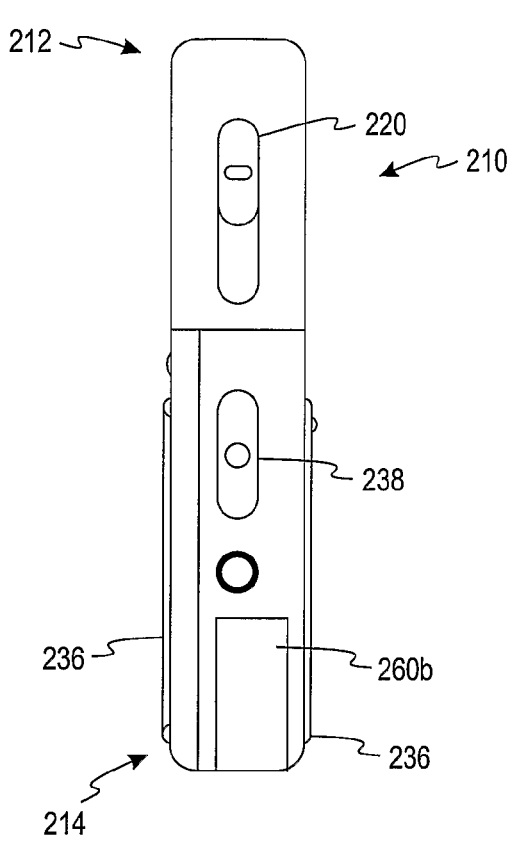
*Fig. 3b*          *Fig. 3c*

SENSOR-DISPENSING INSTRUMENTS

CROSS REFERENCE TO RELATED APPLICATIONS

This application claims priority to Application Ser.No. 60/635,667 filed on Dec. 13, 2004, which is incorporated by reference in its entirety.

FIELD OF THE INVENTION

The present invention generally relates to sensor-dispensing instruments and, more particularly, to sensor-dispensing instruments that are used in determining the concentration of an analyte (e.g., glucose) in a fluid.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check the glucose level in their body fluids to regulate the glucose intake in their diets.

The results of such tests can be used to determine what, if any, insulin or other medication needs to be administered. In one type of blood glucose testing system, test sensors are used to test a fluid such as a sample of blood. The test sensor typically contains biosensing or reagent material that will react with blood glucose. The testing end of the sensor is adapted to be placed into the fluid being tested, for example, blood that has accumulated on a person's finger after the finger has been pricked. The fluid is drawn into a capillary channel that extends in the sensor from the testing end to the reagent material by capillary action so that a sufficient amount of fluid to be tested is drawn into the sensor. The fluid then chemically reacts with the reagent material in the sensor. This results in an electrical signal indicative of the glucose level in the fluid being supplied to contact areas located near the rear or contact end of the test sensor.

The test sensors may be stored in the instrument (also referred to as a meter) or, alternatively, may be stored in a separate container from the instrument. Each of such embodiments have advantages and disadvantages. For example, it is desirable for the test sensors to be stored in the instrument such that all of the needed items are located within one device. There, however, are disadvantages in these systems such as the instruments being larger, more difficult for the user to operate and selected components having reliability issues.

It would be desirable to overcome the above-noted shortcoming of existing systems, while providing a simple, easy and user-friendly mechanism for testing the concentration of a desired analyte.

SUMMARY OF THE INVENTION

According to one embodiment, a sensor-dispensing instrument is adapted to determine an analyte concentration of a fluid and comprises a body, a cap, a cartridge, a test-sensor receptacle, a sensor-advancement mechanism, and a lancing device including a lancet. The cap is adapted to move between an open position and a closed position. The cap and body are adapted to correspond with each other to form the closed position. The cartridge contains a plurality of test sensors. The cartridge is located substantially within the cap. The sensor-advancement mechanism is adapted to advance the plurality of test sensors, one at a time, to a position that allows a user to manually remove the test sensor and place the test sensor in the test-sensor receptacle.

According to another embodiment, a sensor-dispensing instrument is adapted to determine an analyte concentration of a fluid and comprises a body, a cap, a cartridge, a test-sensor receptacle, and a sensor-advancement mechanism. The cap is adapted to move between an open position and a closed position. The cap and body are adapted to correspond with each other to form the closed position. The cartridge contains a plurality of test sensors. The cartridge is located substantially within the cap. The sensor-advancement mechanism is adapted to advance the plurality of test sensors, one at a time, to a position that allows a user to manually remove the test sensor and place the test sensor in the test-sensor receptacle.

According to a further embodiment, a sensor-dispensing instrument is adapted to determine an analyte concentration of a fluid and comprises a body, a cap, a cartridge, a test-sensor receptacle, a sensor-advancement mechanism, and a lancing device including a lancet. The cap is adapted to move between an open position and a closed position. The cap and body are adapted to correspond with each other to form the closed position. The cartridge contains a plurality of test sensors. The cartridge is located substantially within the cap. The sensor-advancement mechanism is adapted to automatically advance the plurality of test sensors, one at a time, to the test-sensor receptacle.

According to another embodiment, a sensor-dispensing instrument is adapted to determine an analyte concentration of a fluid and comprises a body, a cap, a cartridge, a test-sensor receptacle, and a sensor-advancement mechanism. The cap is adapted to move between an open position and a closed position. The cap and body are adapted to correspond with each other to form the closed position. The cartridge contains a plurality of test sensors. The cartridge is located substantially within the cap. The sensor-advancement mechanism is adapted to automatically advance the plurality of test sensors, one at a time, to the test-sensor receptacle.

According to one method, a sensor-dispensing instrument is provided that includes a body, a cap, a cartridge, a test-sensor-receptacle, a sensor-advancing mechanism, and a lancing device including a lancet. The cap is adapted to move between an open position and a closed position. The cap and body are adapted to correspond with each other to form the closed position. The cartridge contains a plurality of test sensors. The cartridge is located substantially within the cap. The sensor-advancement mechanism is activated such that the plurality of test sensors is advanced one at a time. The test sensor is manually removed and placed in the test-sensor receptacle. A fluid is generated using the lancet and placed on the test sensor. The analyte concentration of the fluid is determined.

According to another method, a sensor-dispensing instrument is provided that includes a body, a cap, a cartridge, a test-sensor-receptacle, and a sensor-advancing mechanism. The cap is adapted to move between an open position and a closed position. The cap and body are adapted to correspond with each other to form the closed position. The cartridge contains a plurality of test sensors. The cartridge is located substantially within the cap. The sensor-advancement mechanism is activated such that the plurality of test sensors is advanced one at a time. The test sensor is manually removed and placed in the test-sensor receptacle. A fluid is placed on the test sensor. The analyte concentration of the fluid is determined.

According to a further method, a sensor-dispensing instrument is provided that includes a body, a cap, a cartridge, a test-sensor-receptacle, a sensor-advancing mechanism, and a lancing device including a lancet. The cap is adapted to move between an open position and a closed position. The cap and body are adapted to correspond with each other to form the closed position. The cartridge contains a plurality of test sensors. The cartridge is located substantially within the cap. The sensor-advancement mechanism is activated such that the sensor-advancement mechanism automatically advances the plurality of test sensors, one at a time, to the test-sensor receptacle. A fluid is generated using the lancet and placed on the test sensor. The analyte concentration of the fluid is determined.

According to another method, a sensor-dispensing instrument is provided that includes a body, a cap, a cartridge, a test-sensor-receptacle, and a sensor-advancing mechanism. The cap is adapted to move between an open position and a closed position. The cap and body are adapted to correspond with each other to form the closed position. The cartridge contains a plurality of test sensors. The cartridge is located substantially within the cap. The sensor-advancement mechanism is activated such that the sensor-advancement mechanism automatically advances the plurality of test sensors, one at a time, to the test-sensor receptacle. A fluid is placed on the test sensor. The analyte concentration of the fluid is determined.

BRIEF DESCRIPTION OF THE DRAWINGS

FIG. 1b is a side view of the sensor-dispensing instrument of FIG. 1a.

FIG. 1c is a bottom view of the sensor-dispensing instrument of FIG. 1a.

FIG. 2b is a top perspective view of the sensor-dispensing instrument of FIG. 2a.

FIG. 3b is a side view of the sensor-dispensing instrument of FIG. 3a with the cap in a closed position.

FIG. 3c is an opposing side view of the sensor-dispensing instrument of FIG. 3a with the cap in a closed position.

FIG. 4b is a side view of the sensor-dispensing instrument of FIG. 4a.

Figure 1A:
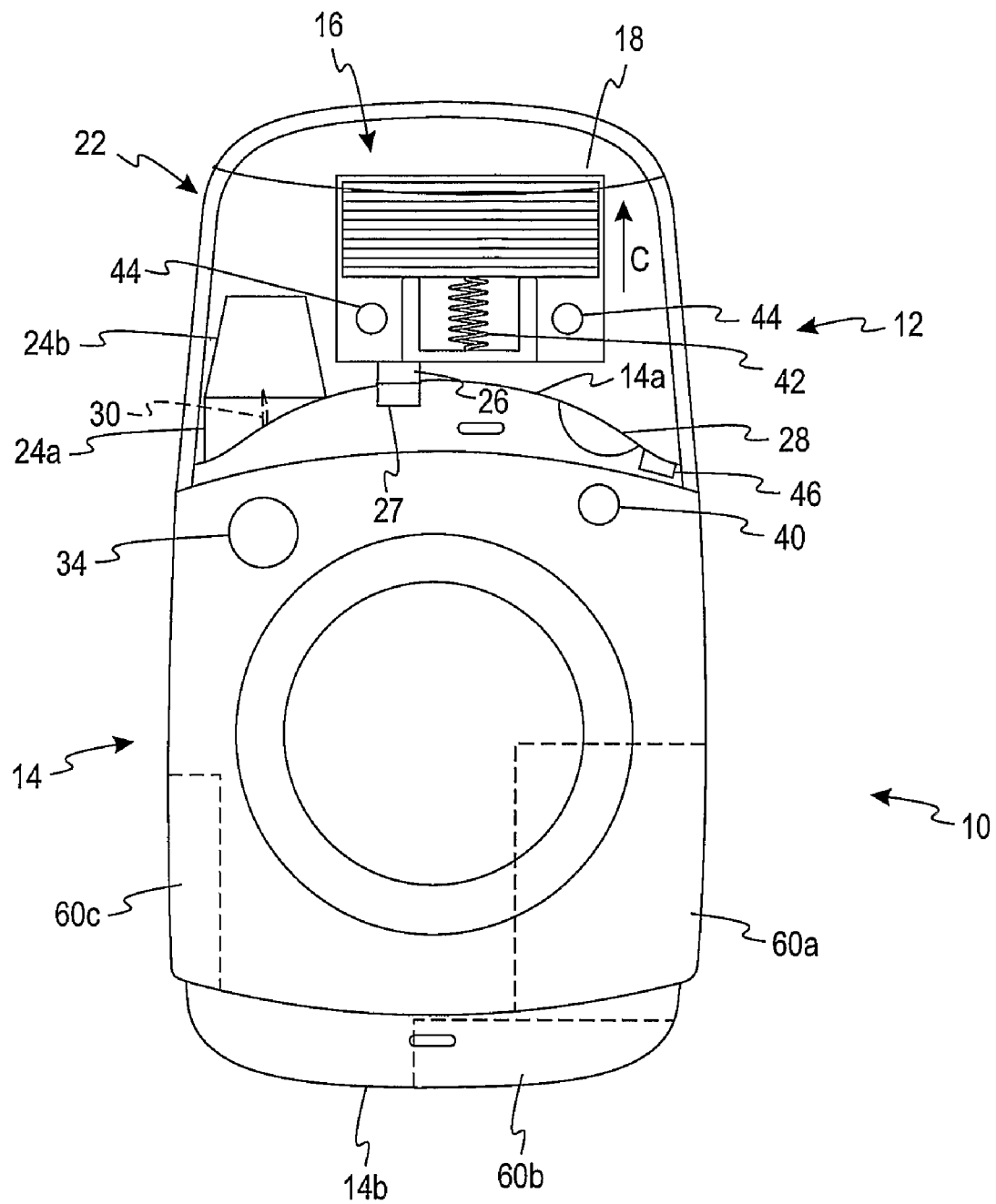
FIG. 1a is a front view of a sensor-dispensing instrument in a closed position according to one embodiment.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention.

DETAILED DESCRIPTION OF THE ILLUSTRATED EMBODIMENTS

The sensor-dispensing instruments of the present invention such as shown in FIGS. 1-4 are used to determine analyte concentrations. Analytes that may be measured using the present invention include glucose, lipid profiles (e.g., cholesterol, triglycerides, LDL and HDL), microalbumin, hemoglobin $A_1C$, fructose, lactate, or bilirubin. The present invention is not limited, however, to these specific analytes and it is contemplated that other analyte concentrations may be determined. The analytes may be in, for example, a whole blood sample, a blood serum sample, a blood plasma sample, or other body fluids like ISF (interstitial fluid) and urine.

Referring to FIGS. 1a-e, a sensor-dispensing instrument 10 is shown according to one embodiment. The sensor-dispensing instrument 10 comprises a cap 12, a body 14, a cartridge 16 that includes a plurality of test sensors 18, and a sensor-advancement mechanism 20.

The cap 12 is adapted to move between an open and a closed position. In the closed position, the cap 12 of FIG. 1a corresponds to the body 14 and desirably forms a snug fit that prevents or inhibits contamination from entering into the sensor-dispensing instrument 10. The cap 12 assists in protecting the cartridge 16, electrical connections in the sensor-dispensing instrument, and a lancing device 24 that includes a lancet 30. The cap 12 may be adapted to correspond to either the top surface 14a of the body 14 (see FIG. 1a) or the bottom surface 14b of the body 14 (see FIG. 1d) as shown in this embodiment.

It is advantageous for a cap to be adapted to attach to the top and bottom surface of the body so as to provide a convenient location to place the cap when the user is performing operations with the sensor-dispensing instrument such as, for example, drawing a bodily fluid, handling a test sensor, or waiting for the determination of an analyte concentration. In such an embodiment, the cap and body are typically not attached or are detachably connected.

The cartridge 16 is located substantially within the cap 12. The cartridge 16 is desirably located entirely within the cap 12, such as shown in FIGS. 1a, 1d. The cartridge 16 contains the plurality of test sensors 18 that is adapted to assist in determining the analyte concentration of the fluid sample. In one embodiment, the plurality of test sensors 18 is stacked horizontally within the cap 12, as shown in FIGS. 1a, 1d. The plurality of test sensors may also be stacked vertically within the cap (see, e.g., plurality of test sensors 118 in FIGS. 2a, 2b). The plurality of test sensors 18 may be adapted for either electrochemical or optical measurement.

Figure 5:
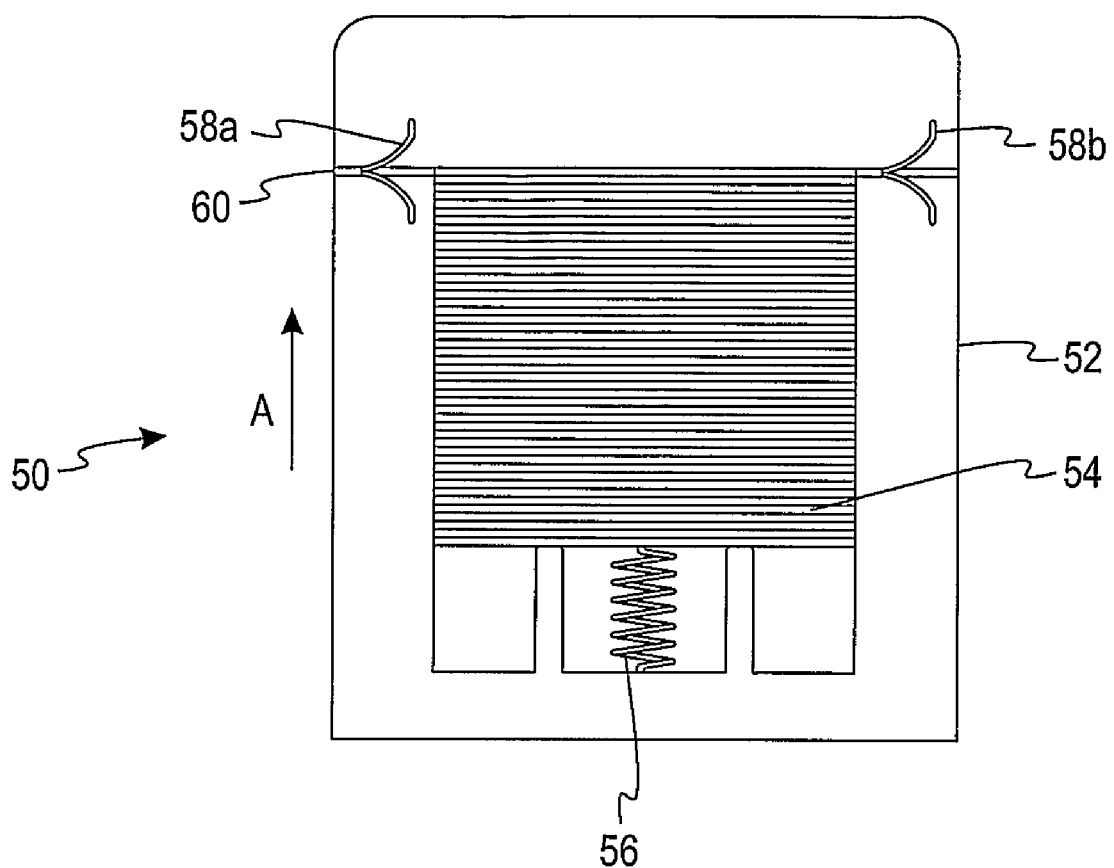
FIG. 5 is a front view of a cartridge according to one embodiment.

Referring to FIG. 5, a cartridge 50 is shown that may be used in the sensor-dispensing instrument 10. The cartridge 50 includes a housing 52 and a plurality of test sensors 54. The plurality of test sensors 54 are moved in the direction of arrow A via a spring 56. The cartridge 50 also includes a plurality of moveable seals 58a,b that protects the plurality of test sensors 54 from the humidity. More specifically, the seals 58a,b prevent or inhibit air and moisture from entering into the interior of the cartridge 50 that contains the plurality of test sensors 54. The plurality of test sensors 54, one at a time, exit the cartridge 50, via an opening 60. The plurality of test sensors 54 may be removed one at a time by using, for example, a pusher assembly to penetrate the moveable seals, contact one of the plurality of test sensors 54 and push or extract one of the test sensors 54 from the cartridge 50 via the opening 60. Such a cartridge, as well as other embodiments of cartridges, are disclosed in Application No. 60/582,712 that was filed on Jun. 24, 2004, and entitled "Cartridge and Sensor-Dispensing Instrument." It is contemplated that other cartridges, which contain the plurality of test sensors, may be used in the sensor-dispensing instrument. The test sensors in other cartridges may be dispensed in a different manner than depicted in FIG. 5.

Referring back to FIGS. 1a-e, the cap 12 includes a flip-lid mechanism 22 that is adapted to move between an open and a closed position. When the flip-lid mechanism 22 is in the open position (see FIG. 1d), the cartridge 16 and the sensor-advancement mechanism 20 are exposed. When the flip-lid mechanism 22 is in an open position, the cartridge can be accessed. It is contemplated that the flip-lid mechanism in the open position may only expose the sensor-advancement mechanism and not the cartridge. The flip-lid mechanism 22 desirably has a snug fit that prevents or inhibits contamination from entering into the sensor-dispensing instrument 110. The flip-lid mechanism may have a seal instead of or in addition to the cartridge for preventing or inhibiting the atmosphere (i.e., moisture) from entering into the cartridge.

The sensor-advancement mechanism 20 is adapted to advance the plurality of test sensors 18 from the cartridge 16 one at a time. The sensor-advancement mechanism 20 of FIG. 1d is moved in the direction of arrow B to advance the plurality of test sensors 18 from the cartridge 16 one at a time. The sensor-advancement mechanism 20 may, for example, be a variety of mechanisms extract the plurality of test sensors 18, one at a time, from the cartridge 16. The plurality of test sensors 18 may be pulled or pushed from the cartridge 16.

To assist in positioning the next one of the plurality of test sensors to be extracted, at least one spring 42 may be used that moves the plurality of test sensors 18 in the direction of arrow C in FIG. 1a.

When the flip-lid mechanism 22 is in the open position, the user may advance one of the plurality of test sensors 18, or replace the cartridge 16. In the closed position, the flip-lid mechanism 22 protects (a) against inadvertent advancement of one the plurality of test sensors 18, and (b) the plurality of test sensors 18 from being exposed to the environment.

To protect the plurality of test sensors, desiccant material 44 is desirably added to the cartridge 16 to assist in maintaining an appropriate humidity level within the interior thereof that contains the plurality of test sensors 18. By maintaining an appropriate humidity level, reagent material in the test sensors, if used, is protected. The amount of desiccant material 44 should be sufficient to obtain the desired shelf-life (the time period before any of the plurality of test sensors are used). The amount of desiccant material 44 should also be sufficient to obtain the desired use-life (the time period after first use of one of the plurality of test sensors).

The desiccant may be in the form of several shapes including balls, tablets, granular, or paper. For example, the desiccant may be molecular sieve spheres or thick desiccant paper. The desiccant may be placed within the cartridge 16 as shown with desiccant material 44. The desiccant may be molded into an interior surface of the housing of the cartridge 16 so as to absorb moisture within the same. One non-limiting example of desiccant material may be purchased from Multisorb of Buffalo, N.Y. in the form of, for example, molecular sieve beads.

To allow viewing of the remaining ones of the test sensors 18, the cap 12 of the sensor-dispensing instrument 10 is typically translucent. The cap 12, however, may be adapted to allow viewing of the plurality of test sensors 18 by having the cap 12 form a window.

The cartridge 16 also includes a calibration information device 26 (see FIG. 1a) that contains information about the plurality of test sensors 18 and is used to assist in calibrating the sensor-dispensing instrument 10. The calibration information device 26 is typically connected to a calibration read mechanism 27 of the instrument 10. The calibration information device 26 may contain calibration information such as sensitivity to the reagent or temperature profiles, date of manufacture, and date of expiration. The device 26 may be in the form of a memory device such as an EPROM, an electrical barcode-type label, an optical barcode-type label, an RF label or other forms that are adapted to store or convey calibration information. The electrical barcode-type label may be a plurality of electrical contacts that is connected to the calibration read mechanism and conveys information about the calibration based on a programmed conductive pattern. Using a calibration information device such as an optical barcode-type label or an RF label does not require the use of a physical connection to a calibration read mechanism.

The information may be read optically or electronically. The sensor-dispensing instrument 10 may be adapted to calibrate upon closure of the cap 12.

The cap 12 may be disposable such that the user disposes of the cap 12 after each of the plurality of test sensors 18 has been used. Subsequently, a user would typically place a second identical cap that includes a cartridge with a plurality of unused test sensors. Alternatively, the cap 12 may be reusable with only the cartridge 16 being disposed of after the plurality of test sensors has been used. In such an embodiment, after each of the plurality of test sensors 18 has been used, the user removes the cartridge 16 from the cap 12 of the sensor-dispensing instrument 10 and replaces it with a second identical cartridge that includes a plurality of unused test sensors.

The body 14 of the sensor-dispensing instrument 10 includes a test-sensor receptacle 28. To prepare the sensor-dispensing instrument 10 for testing, according to one method, the cap 12 is placed in the open position, which exposes the lancing device 24 and the test-sensor receptacle 28. The cap 12 may then be attached to the bottom surface 14b of the body 14 for convenience. The flip-lid mechanism 22 (see FIG. 1d) is opened to expose the sensor-advancement mechanism 20 and the plurality of test sensors 18.

The user slides the sensor-advancement mechanism 20 causing one of the plurality of test sensors 18 to advance from the cartridge 16. It is contemplated that the user may activate the sensor-advancement mechanism 20 by other methods such as pressing a button or pulling the plurality of test sensors 18 from the stack by hand.

The user then manually grasps and places the test sensor in the test-sensor receptacle 28. The test-sensor receptacle 28 may be situated at an angle, such as in FIGS. 1a, 1e to facilitate alternate site testing and easier loading. For example, a test sensor 18a is shown situated at an angle in the test-sensor receptacle 28 in FIG. 1e. It is contemplated, however, that the test-sensor receptacle 28 may be generally perpendicular or perpendicular to the top surface 14a of the body 14.

Figure 1B:
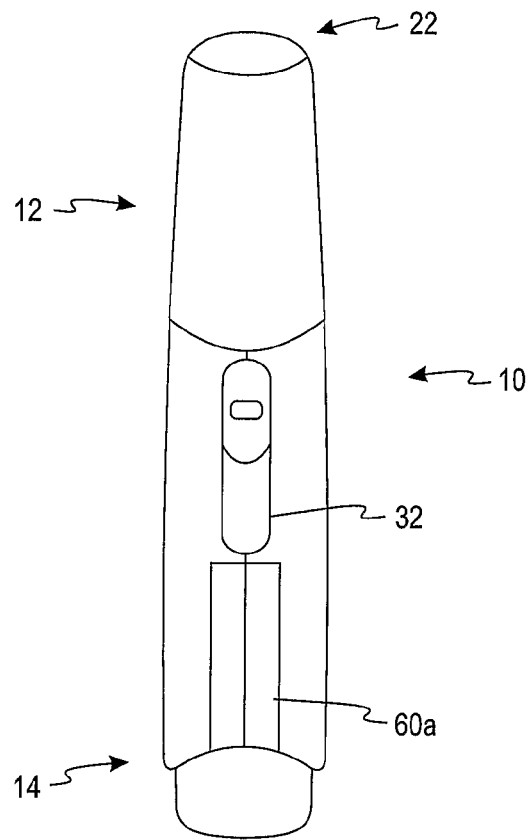
Figure 1C:
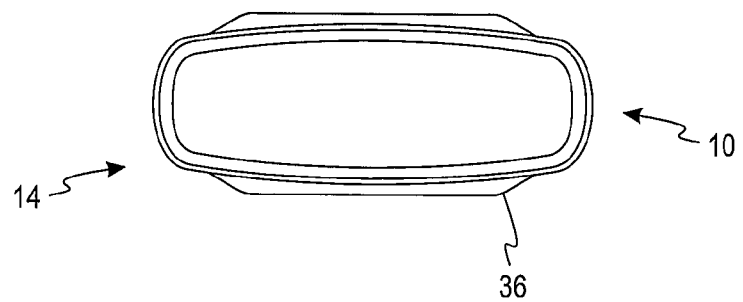
Figure 1D:
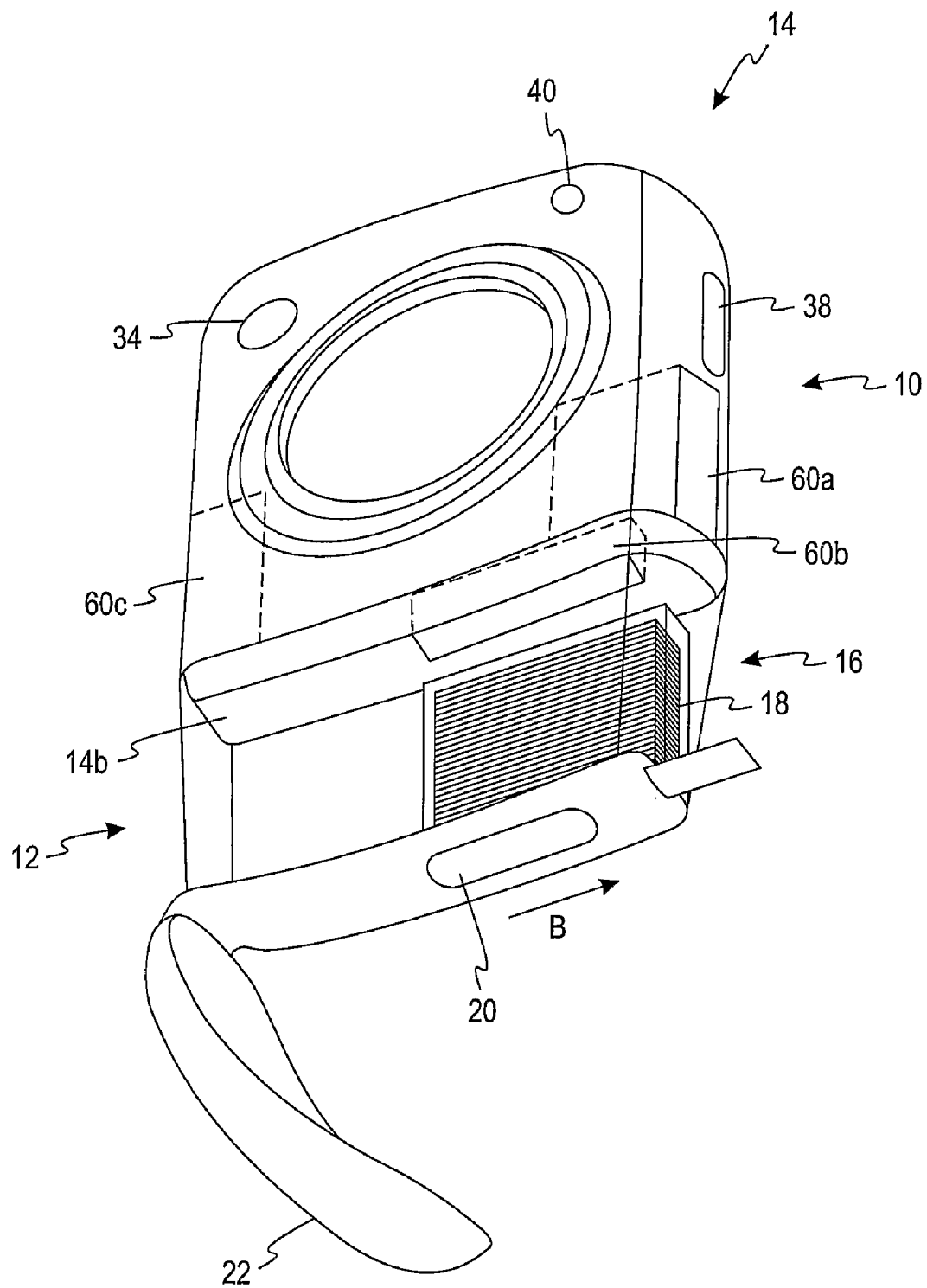
FIG. 1d is a bottom perspective view of the sensor-dispensing instrument of FIG. 1a in an open position.
Figure 1E:
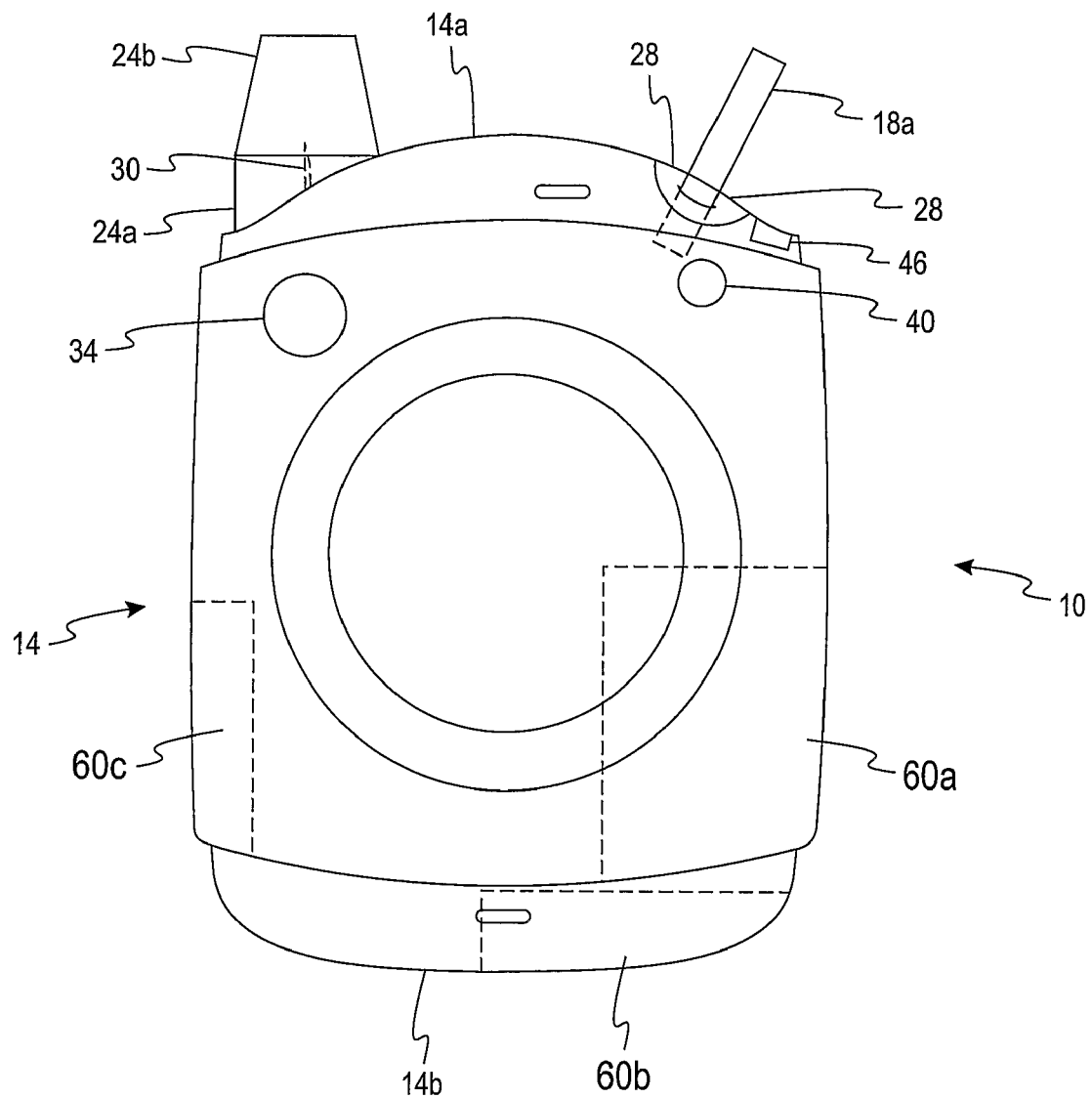
FIG. 1e is a front view of the sensor-dispensing instrument of FIG. 1a in an open position with a test sensor being inserted.

Referring to FIGS. 1a, 1e, the body 14 of the sensor-dispensing instrument 10 depicts the lancing device 24 that includes (a) the lancet 30, (b) a lancing portion 24a that holds the lancet 30, and (c) a lancing endcap 24b that protects the user from inadvertently contacting the lancet 30. The lancet 30 is adapted to obtain a fluid sample from the user. The lancet 30 is typically retractable. The lancing device 24 is adjacent to the test-sensor receptacle 28 for convenient side-by-side lancing and testing that reduces the required level of component manipulation by the user. It is contemplated, however, that the lancing device and the test-sensor receptacle may be located in different positions with respect to each other.

As shown in FIGS. 1a, 1b, the body 14 includes a cocking device 32 and a firing mechanism 34. According to one embodiment, the cocking device 32 is used to prepare the lancing device 24 for firing, and the firing mechanism 34 fires the lancet 30 via the lancing device 24. The cocking device 32 and firing mechanism 34 may be separate, as shown in FIGS. 1a, 1b, or combined together.

To provide enhanced storage options to a user, the body 14 may form a storage compartment 36 such as shown in FIG. 1c that is adapted to store a plurality of lancets, additional cartridges, test sensors and/or other items. Thus, the user may conveniently carry a sensor-dispensing instrument that includes replacement components of the system.

The storage compartment 36 may be referred to as self-contained storage since the storage compartment 36 is located within the sensor-dispensing instrument 10. Additionally, the components to be stored in the storage compartment 36 may be used components or replacement components such as lancets, cartridges and test sensors. This allows for easier transport and/or storage of necessary testing supplies as well as a discrete way to dispose of used supplies until permanent discarding is desired. The used components are typically stored until a more permanent waste container is accessible. The storage compartment 36 may further include additional items such as desiccant if, for example, test sensors are being stored. To prevent or inhibit contamination, it is desirable to have separate storage areas for the used and replacement components. It is also desirable to have a hygienic sleeve for the storage compartment or portion thereof that is adapted to contain used components.

The storage compartment 36 shown in FIG. 1c is permanently formed by the body 14. It is contemplated that a storage compartment may be detachably added to the body. Thus, in such an embodiment, the storage compartment is removable by the user. Such a storage compartment may include used components or replacement components such as lancets, cartridges and test sensors as discussed above.

Furthermore, the storage compartment does not need to be in the exact location depicted in FIG. 1c. For example, the storage compartments may be formed in other locations within the body 14 or even the cap 12. As shown in FIG. 1a, storage compartments 60a-c are shown as being formed within the body 14. As discussed above, the storage compartments 60a-c may include used components or replacement components such as lancets, cartridges and test sensors as discussed above. It is contemplated that there may be less or more of the storage compartments than shown in FIG. 1a. The storage compartments 60a-c may be used in addition to, or instead of, the storage compartment 36.

The sensor-dispensing instrument 10 may include a detection mechanism that detects whether the cap and/or flip lid is in a closed position. For example, the sensor-dispensing instrument may include a detection mechanism 46 such as a contact switch that alerts the user when the cap is not in the closed position. This alert may be provided to the user via an audible signal. This is especially desirable if the cap in the closed position provides the main source of protecting the test sensors from being exposed to humidity from the environment. The cap 12 may also be designed to provide a seal that assists in preventing or inhibiting moisture from being exposed to the plurality of test sensors 18.

The sensor-dispensing instrument 10, as shown in FIG. 1d, includes a navigation control 38 that is adapted to navigate the testing and test-result options available to the user. Additionally, referring to FIGS. 1a, 1d, the sensor-dispensing instrument 10 includes an ejection mechanism 40 that is adapted to release one of the plurality of test sensors 18 after testing.

Ejection may be accomplished by several methods. In one method, the sensor-dispensing instrument may include an ejection mechanism that ejects the used test sensor from the sensor-dispensing instrument. In such an embodiment, the test sensor is released forcefully. In another method, the test sensors may be ejected by (a) releasing a grip of the test sensors, and (b) tipping the sensor-dispensing instrument such that the test sensor falls from the test-sensor receptacle via gravity. In a further method, the test sensor may also be removed manually from the sensor-dispensing instrument by grasping and pulling the test sensor from the sensor-dispensing instrument.

The plurality of test sensors utilized by the sensor-dispensing instrument is typically provided with a capillary channel that extends from the front or testing end of the sensors to biosensing or reagent material disposed in the sensor. When the testing end of the sensor is placed into fluid (e.g., blood that is accumulated on a person's finger after the finger has been pricked by the lancet), a portion of the fluid is drawn into the capillary channel by capillary action. The fluid then chemically reacts with the reagent material in the test sensor so that an electrical signal indicative of the analyte concentration (e.g., glucose concentration) in the fluid is supplied and subsequently transmitted to an electrical assembly.

The results of the analysis may then be displayed such as on a liquid crystal display of the sensor-dispensing instrument. Some of the information that may be displayed when the sensor-dispensing instrument include the following: a battery indication, a numerical display, an indication of the number of sensors remaining, an indication to load a cartridge into the sensor-dispensing instrument, apply blood indication, a temperature indication, or various combinations thereof. It is contemplated that other types of displays may be used.

According to one testing process, a whole blood sample may be prepared for testing by (a) advancing one of the test sensors and manually placing the test sensor in the test-sensor receptacle to receive a whole blood sample; (b) generating a whole blood sample via the lancing device; and (c) bringing the test sensor and the whole blood sample into contact wherein the blood is generally drawn into the sensor by capillary action.

Figure 2A:
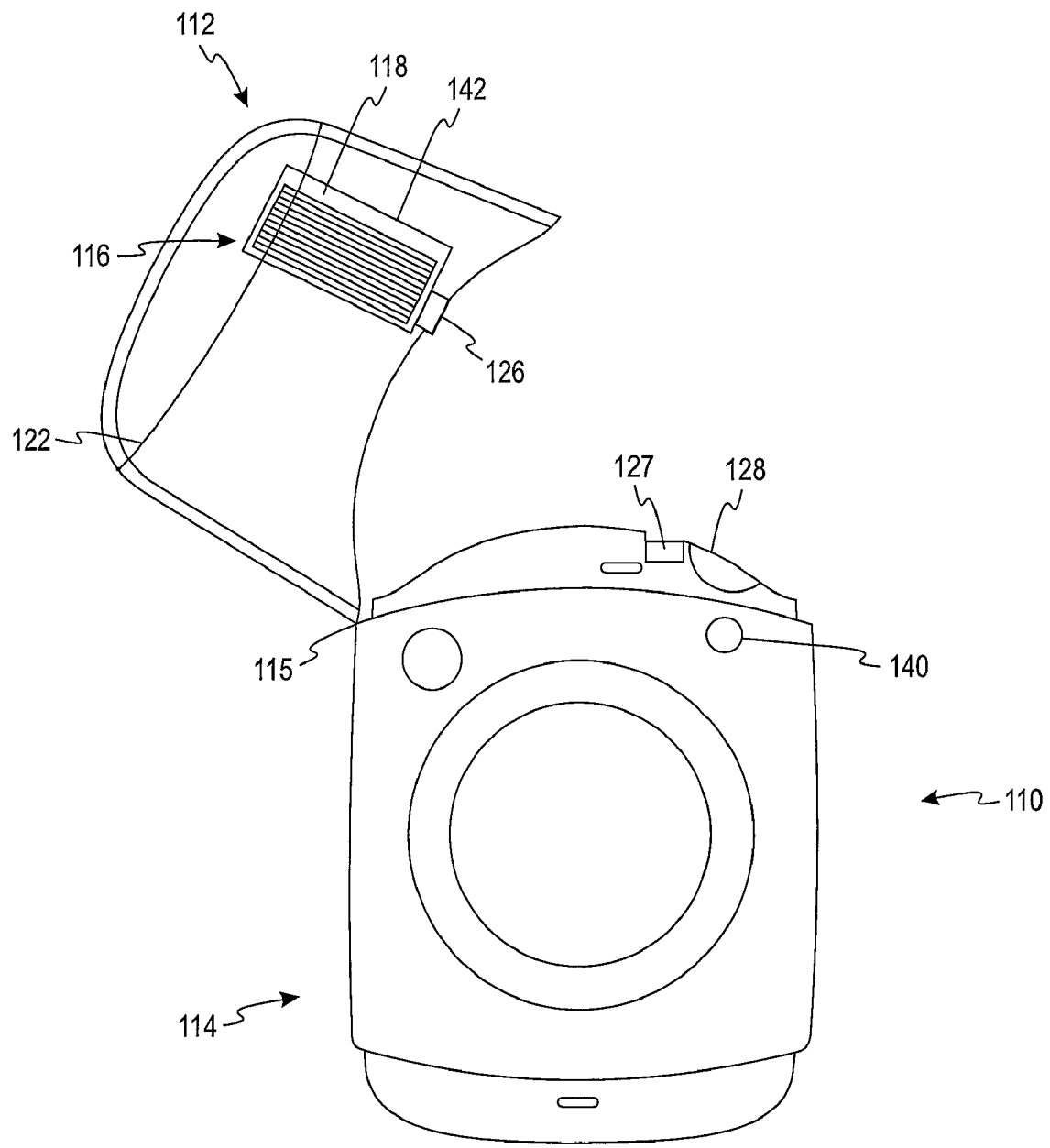
FIG. 2a is a front view of a sensor-dispensing instrument in a open position according to another embodiment.
Figure 2B:
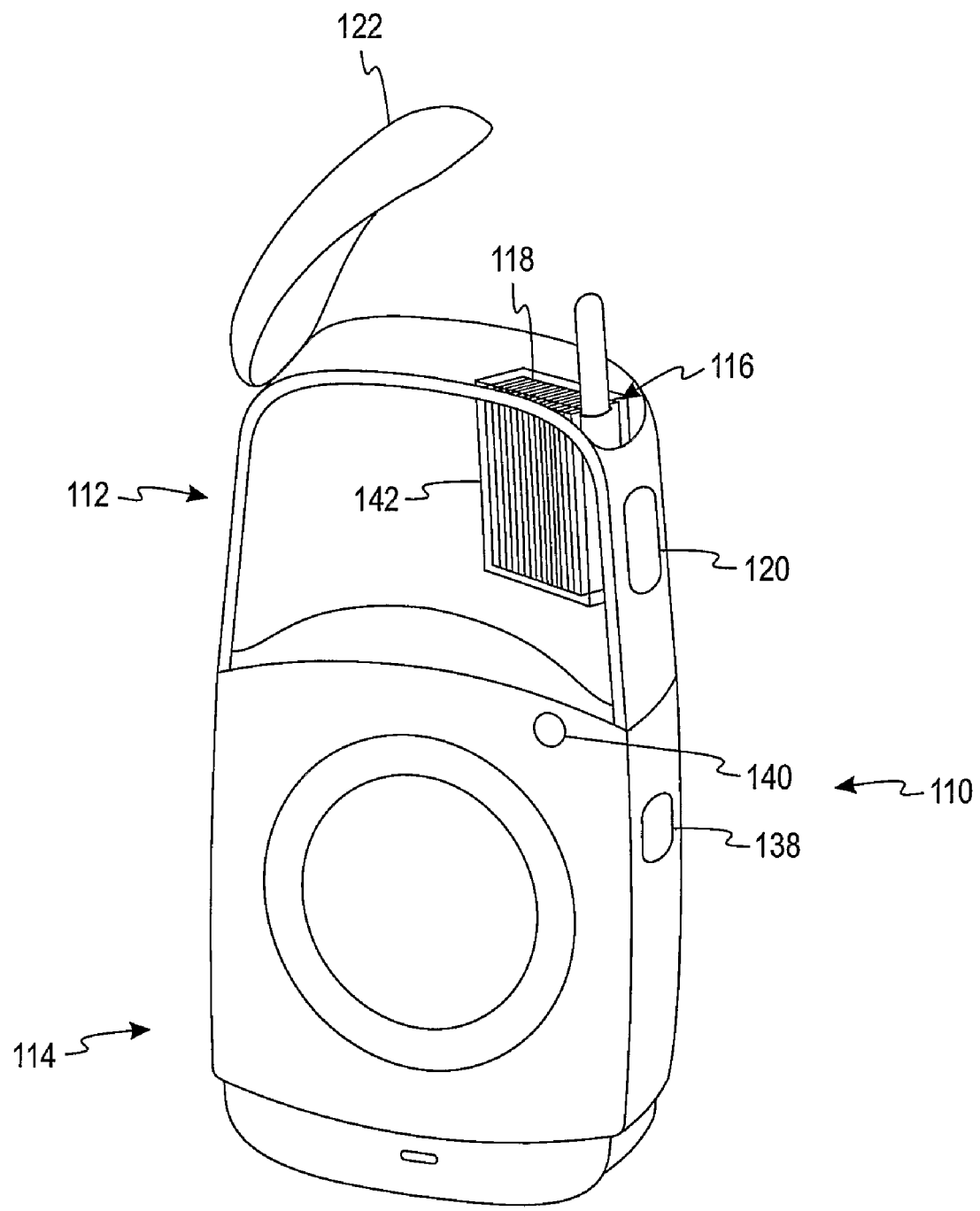

FIGS. 2a, 2b illustrate a sensor-dispensing instrument according to another embodiment. The sensor-dispensing instrument 110 of FIGS. 2a, 2b includes some similar features to the sensor-dispensing instrument 10 of FIGS. 1a-e. The sensor-dispensing instrument 110 comprises a cap 112, a body 114, a cartridge 116 that includes the plurality of test sensors 118, and a sensor-advancement mechanism 120. The sensor-dispensing instrument 110 of FIGS. 2a, 2b, however, does not include, for example, a lancing device, cocking device, firing mechanism, or storage space for a plurality of lancets as depicted in the sensor-dispensing instrument 10 of FIGS. 1a-e.

The cap 112 is adapted to move between an open and a closed position. In the closed position, the cap 112 corresponds to the body 114 and desirably forms a snug fit that prevents or inhibits contamination from entering into the sensor-dispensing instrument 110. As shown in FIG. 2a, the cap 112 is attached to the body 114 of the sensor-dispensing instrument 110 via a hinge 115. It is advantageous for a cap to be attached to the body via a hinge so as to secure the cap when the user is performing operations with the sensor-dispensing instrument such as, for example, handling the test sensor or waiting for the analyte concentration to be determined. Since the cap 112 and the body 114 are attached via the hinge 115, it may be desirable for the cap 112 to be reused and the cartridge to be disposable. It is contemplated, however, that the cap and the body may be detachable connected via the hinge such that the cap may be disposable.

The cap 112 of FIGS. 2a, 2b includes the sensor-advancement mechanism 120, the cartridge 116, a flip-lid mechanism 122, and a window 142 adapted to allow viewing of the remaining plurality of test sensors 118. The cap, however, may also be opaque, or adapted to allow viewing of the plurality of test sensors by other methods. The plurality of test sensors 118 is adapted for either electrochemical or optical measurement. As shown in FIGS. 2a, 2b, the plurality of test sensors 118 is stacked vertically in the cap 112. The cartridge 116 includes a calibration information device 126 that is adapted to store or convey calibration information to a calibration read mechanism 127 of the instrument 110. It is contemplated that other cartridges may be used in the sensor-dispensing instrument 110.

The body 114 of the sensor-dispensing instrument 110 of FIGS. 2a, 2b includes a test-sensor receptacle 128, an ejection mechanism 140, and a navigation control 138. To prepare the sensor-dispensing instrument 110 for testing, according to one method, the user slides the sensor-advancement mechanism 120 causing one of the plurality of test sensors 118 to advance from the cartridge 116. It is contemplated that the user may activate the sensor-advancement mechanism 120 by other methods such as pressing a button. The user then manually places the test sensor in the test-sensor receptacle 128. It is contemplated that the body 114 may be designed to include a storage space for lancets, such as storage compartment 36 and storage compartments 60a-c discussed above in FIGS. 1a, 1c.

Referring to FIGS. 3a-d, a sensor-dispensing instrument is shown according to a further embodiment. A sensor-dispensing instrument 210 of FIGS. 3a-d comprises a cap 212, a body 214, a cartridge 216 that includes a plurality of test sensors 218, and a sensor-advancement mechanism 220.

Figure 3A:
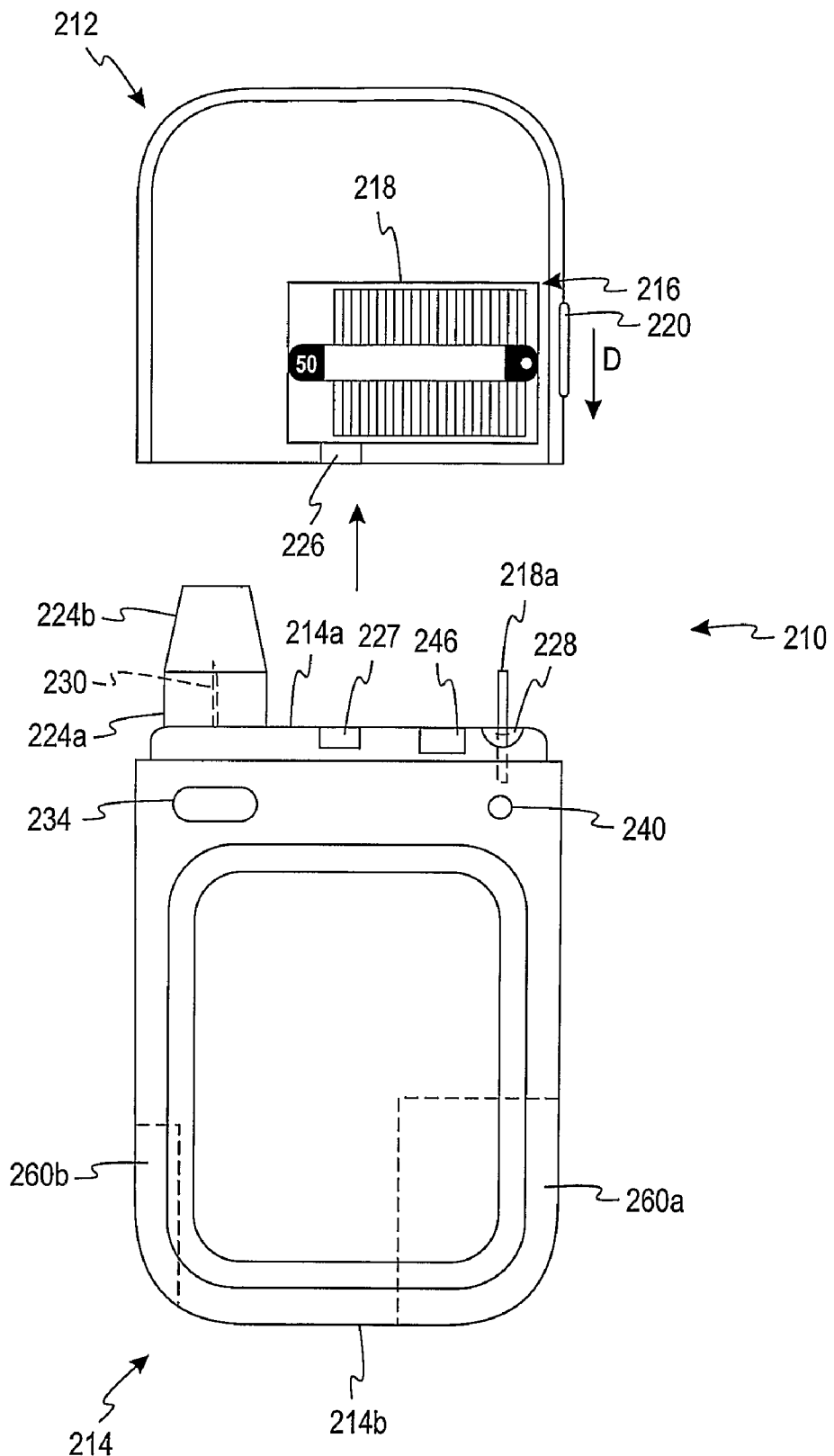
FIG. 3a is a front view of a sensor-dispensing instrument with a cap in an open position according to a further embodiment.
Figure 3D:
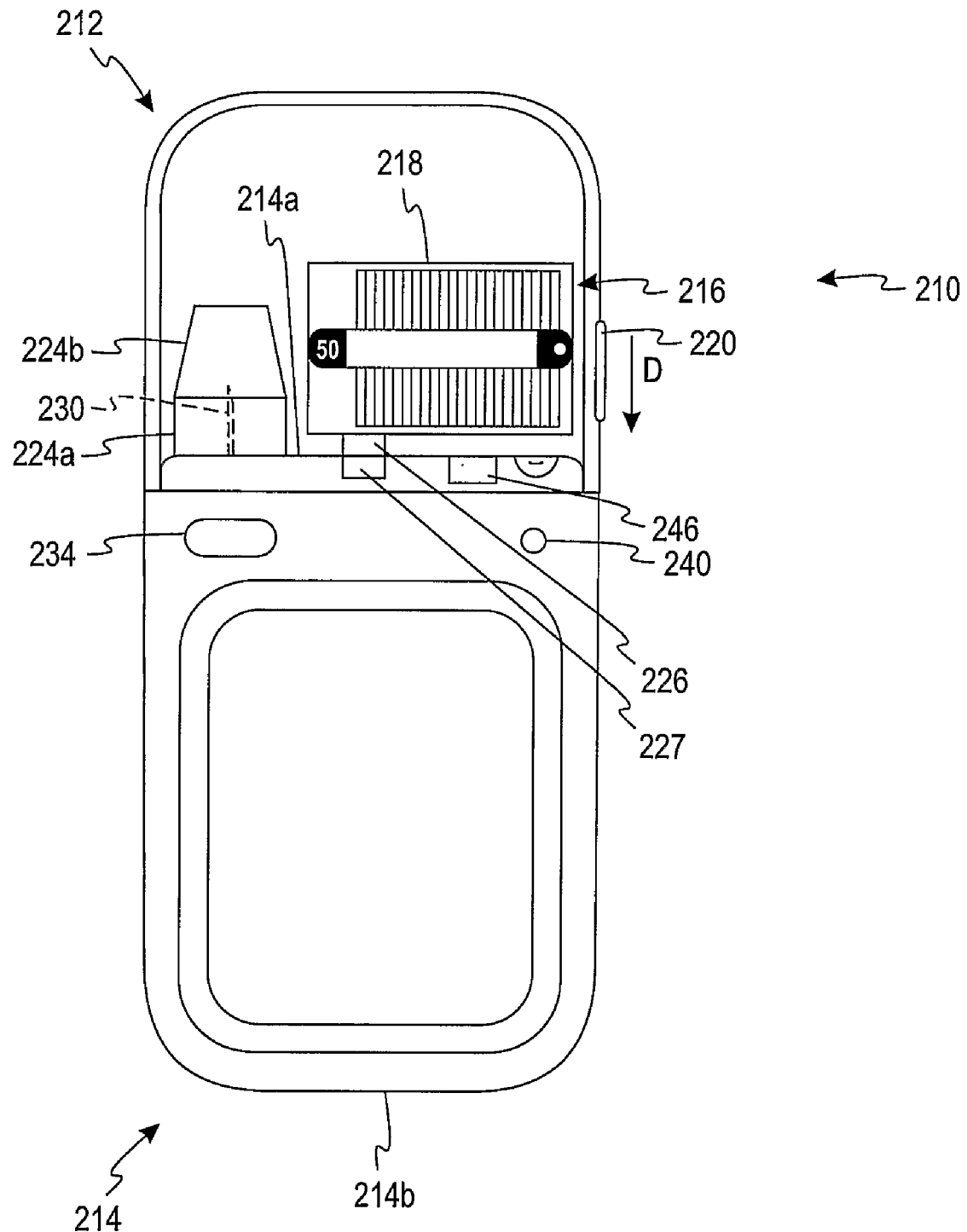
FIG. 3d is a front view of the sensor-dispensing instrument of FIG. 3a with the cap in a closed position.

The cap 212 is adapted to move between an open and a closed position. In the closed position of FIG. 3d, the cap 212 corresponds to the body 214 and desirably forms a snug fit that prevents or inhibits contamination from entering the sensor-dispensing 210. The cap 212 of FIG. 3a is removable from the body 214 and may be adapted to correspond to either a top surface 214a or a bottom surface 214b of the body 214.

It is advantageous for a cap to be adapted to attach to the top and bottom surfaces of the body so as to provide a convenient location to place the cap when the user is performing operations with the sensor-dispensing instrument such as, for example, drawing a bodily fluid or waiting for the analyte concentration to be determined. In such an embodiment, the cap and body are typically not attached or are detachably connected.

The cartridge 216 is located substantially within the cap 212. The cartridge 216 is desirably located entirely within the cap 212 as shown, for example, in FIG. 3a. The cartridge 216 contains the plurality of test sensors 218 that is adapted to assist in determining the analyte concentration of the fluid sample. As shown in the embodiment of FIG. 3a, the plurality of test sensors 218 is stacked vertically in the cap 212. The plurality of test sensors 218 is adapted for either electrochemical or optical measurement.

As noted previously, the cap 212 is adapted to move between an open and a closed position. When the cap 212 is detached from the body 214 (i.e., in an open position), a lancing device 224, the cartridge 216, and a test-sensor receptacle 228 are exposed and accessible. The cartridge 216 (see FIG. 3a) includes a calibration information device 226 as discussed above that is adapted to store or convey calibration information to a calibration read mechanism 227 of the instrument 210. The sensor-advancement mechanism 220 is adapted to advance the plurality of test sensors 218 from the cartridge 216 one at a time. In the open position, the user may replace the cartridge 216 according to one embodiment. In the closed position, the cap 212 protects the test-sensor receptacle 228, the calibration read mechanism 227 and the lancing device 224. The cap 212 may also be designed to provide a seal that assists in preventing or inhibiting moisture from being exposed to the plurality of test sensors 218.

To allow viewing of the remaining ones of the plurality of test sensors 218, the cap 212 of the sensor-dispensing instrument 210 of FIGS. 3a-d is typically translucent. The cap 212, however, may be adapted to allow viewing of the plurality of test sensors 218 by having the cap 212 form a window. The sensor-dispensing instrument 210 may be adapted to calibrate upon closure of the cap 212.

The cap 212 may be disposable such that the user disposes of the cap 212 after each of the plurality of test sensors 218 has been used. Subsequently, a user would typically place a second identical cap that includes a cartridge with a plurality of unused test sensors. Alternatively, the cap 212 may be reusable with only the cartridge 216 being disposed after the plurality of test sensors has been used. In such an embodiment, after each of the plurality of test sensors 218 has been used, the user removes the cartridge 216 from the cap 212 of the sensor-dispensing instrument 210 and replaces it with a second identical cartridge that includes a plurality of unused test sensors.

The body 214 of the sensor-dispensing instrument 210 includes the test-sensor receptacle 228. To prepare the sensor-dispensing instrument 210 for testing, according to one method, the sensor-dispensing instrument 210 is placed in a closed position (see FIG. 3d). During the closed position, the user slides the sensor-advancement mechanism 220 causing one of the plurality of test sensors 218 to advance from the cartridge 216. The plurality of test sensors 218 is moved one at a time in the direction of arrow D. The sensor-dispensing instrument 210 automatically moves one of the test sensors 218 into the test-sensor receptacle 228 without any manual handling of the test sensor. It is advantageous for the sensor-advancement mechanism 220 to place the test sensors 218, one at a time, directly into the test-sensor receptacle 228 so as to reduce the requisite amount of user manipulation. To continue the testing process, the user removes the cap 212 from the body 214 (see open position of FIG. 3a). FIG. 3a shows the automatically placed test sensor 218a in the test-sensor-receptacle 228.

Referring still to FIG. 3a, the body 214 of the sensor-dispensing instrument 210 includes the lancing device 224 that includes (a) a lancet 230, (b) a lancing portion 224a that holds the lancet 230, and (c) a lancing endcap 224b that covers and protects the user from inadvertently contacting the lancet 230. In the sensor-dispensing instrument 210 of FIG. 3a, the lancing device 224 is adjacent to the test-sensor receptacle 228 for convenient side-by-side lancing and testing that reduces the required level of component manipulation by the user. It is contemplated, however, that the lancing device and the test-sensor receptacle may be located in different positions with respect to each other.

As shown in FIGS. 3a, 3b, the body 214 includes a cocking device 232 and a firing mechanism 234. According to one embodiment, the cocking device 232 is used to prepare the lancing device 224 for firing, and the firing mechanism 234 fires the lancet 230 via the lancing device 224. Before the firing mechanism 234 fires the lancet 230, the lancing endcap 224b is removed from the lancing portion 224a to expose the lancet 230. The cocking device 232 and firing mechanism 234 may be separate, as shown in FIGS. 3a, 3b, or combined together.

To provide enhanced storage options to a user, the body 214 forms a storage compartment 236 (see FIGS. 3b, 3c) that is adapted to store a plurality of lancets, additional cartridges, test sensors and/or other items. Thus, the user may conveniently carry a sensor-dispensing instrument that includes replacement components of the system.

The storage compartment 236 may be referred to as self-contained storage. Additionally, the components to be stored in the storage compartment 236 may be used components or replacement components such as lancets, cartridges and test sensors. The storage compartment 236 may further include additional items such as desiccant if, for example, test sensors are being stored. To prevent or inhibit contamination, it is desirable to have separate storage areas for the used and replacement components. It is also desirable to have a hygienic sleeve for the storage compartment or portion thereof that is adapted to contain used components. The used components are typically stored until a more permanent waste container is accessible.

The storage compartment 236 shown in FIGS. 3b, 3c is permanently formed by the body 214. It is contemplated that a storage compartment may be detachably added to the body. Thus, in such an embodiment, the storage compartment is removable by the user. Such a storage compartment may include used components or replacement components such as lancets, cartridges and test sensors as discussed above.

Furthermore, the storage compartment does not need to be in the exact location depicted in FIGS. 3b, 3c. For example, the storage compartments may be formed in other locations within the body 214 or even the cap 212. As shown in FIG. 3a, storage compartments 260a, 260b are shown as being formed within the body 14. As discussed above, the storage compartments 260a, 260b may include used components or replacement components such as lancets, cartridges and test sensors as discussed above. It is contemplated that there may be less or more of the storage compartments than shown in FIG. 3a. The storage compartments 260a, 260b may be used in addition to, or instead of, the storage compartment 236.

The sensor-dispensing instrument 210 may include a detection mechanism that detects whether the cap is in a closed position. For example, the sensor-dispensing instrument may include a detection mechanism 246 such as a contact switch that alerts the user when the cap is not in the closed position. This alert may be provided to the user via an audible signal. This is especially desirable if the cap in the closed position provides the main source of protecting the test sensors from being exposed to humidity from the environment.

The sensor-dispensing instrument 210 includes a navigation control 238 (see FIG. 3c) that is adapted to navigate the testing and test-result options available to the user. Additionally, referring to FIG. 3a, the sensor-dispensing instrument 210 includes an ejection mechanism 240 that is similar to described above with the ejecting mechanism 40. Ejection of a test sensor from the sensor-dispensing instrument may be accomplished in a similar manner as discussed above with respect to the sensor-dispensing instrument 10 of FIG. 1.

Figure 4A:
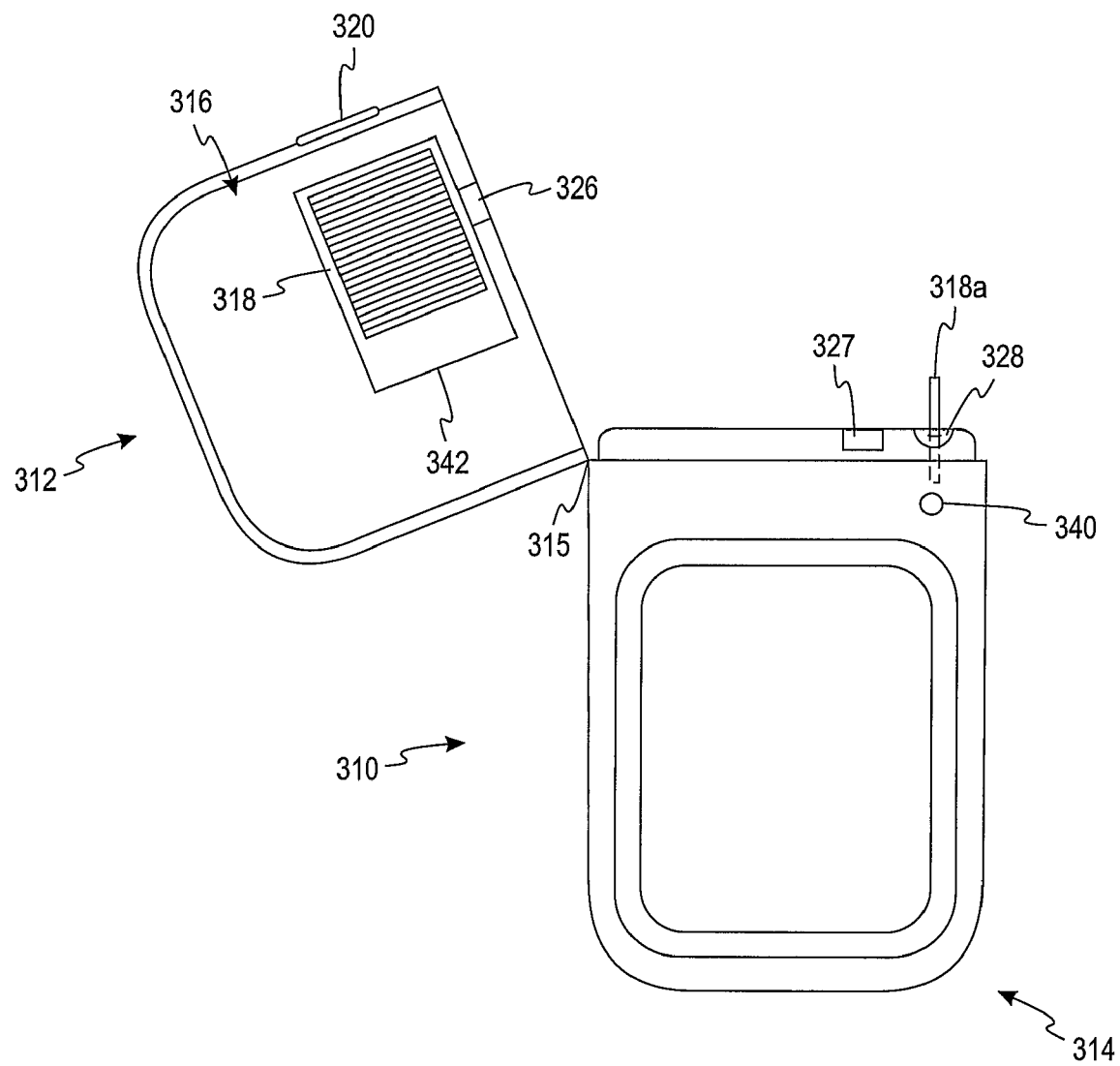
FIG. 4a is a front view of a sensor-dispensing instrument in an open position according to yet another embodiment.
Figure 4B:
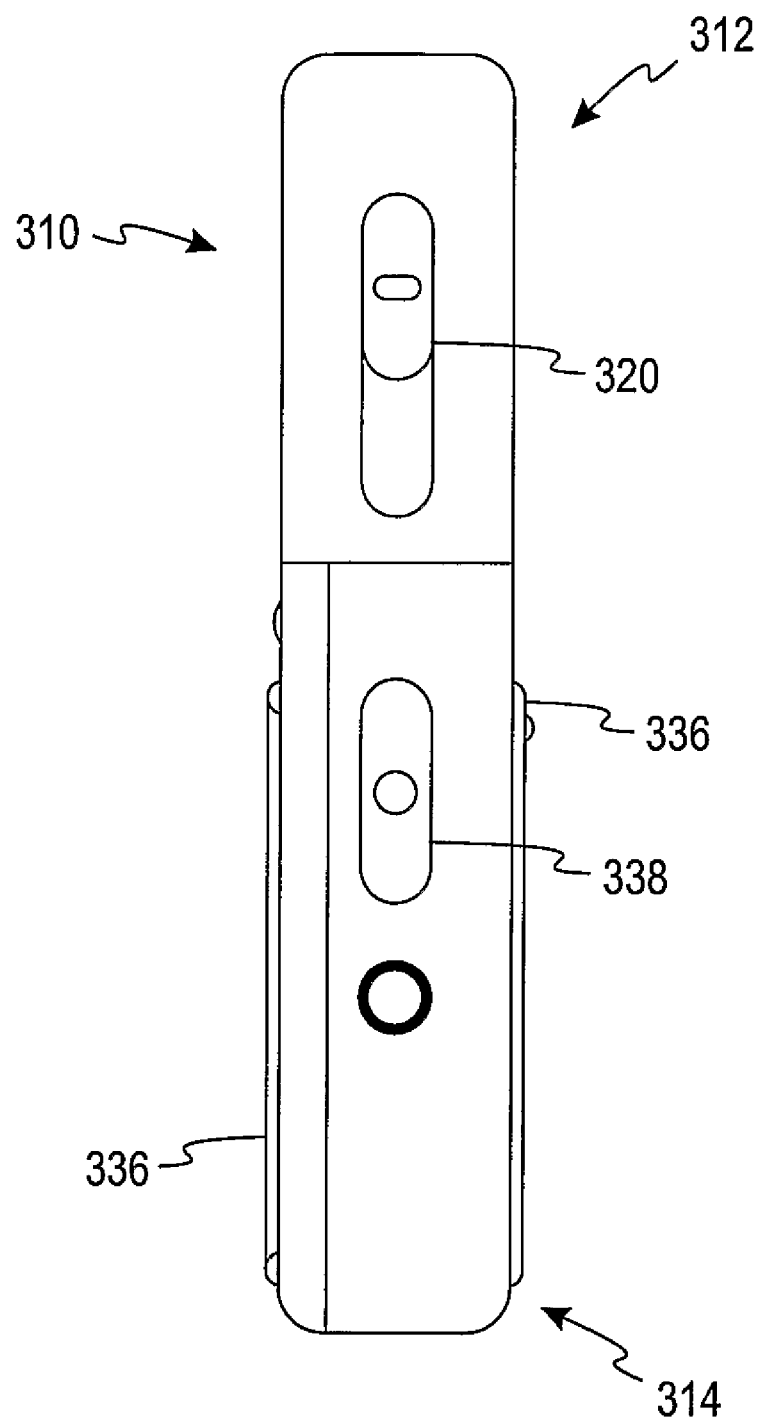

FIGS. 4a, 4b illustrate a sensor-dispensing instrument according to another embodiment. The sensor-dispensing instrument 310 includes some similar features to the sensor-dispensing instrument 210 of FIGS. 3a-d. The sensor-dispensing instrument 310 of FIGS. 4a, 4b comprises a cap 312, a body 314, a cartridge 316 that includes a plurality of test sensors 318, and a sensor-advancement mechanism 320. The sensor-dispensing instrument 310 of FIGS. 4a, 4b, however, does not include, for example, a lancing device, cocking device, or firing mechanism as depicted in the sensor-dispensing instrument 210 of FIGS. 3a-d.

The cap 312 is adapted to move between an open and a closed position. In the closed position, the cap 312 corresponds to the body 314 and desirably forms a snug fit that prevents or inhibits contamination from entering into the sensor-dispensing instrument 310. As shown in FIG. 4a, the cap 312 is attached to the body 314 of the sensor-dispensing instrument 310 via a hinge 315. It is advantageous for a cap to be attached to the body via a hinge so as to secure the cap when the user is performing operations with the sensor-dispensing instrument such as, for example, waiting for the analyte concentration to be determined.

The cap 312 includes the sensor-advancement mechanism 320, the cartridge 316 and a window 342 adapted to allow viewing of the plurality of test sensors 318. The plurality of test sensors 318 is adapted for either electrochemical or optical measurement. The cartridge 316 (see FIG. 4a) includes a calibration information device 326 as discussed above that is adapted to store or convey calibration information to a calibration read mechanism 327 of the instrument 310.

The body 314 of the sensor-dispensing instrument 310 of FIGS. 4a-b includes a test-sensor receptacle 328, a storage compartment 336, an ejection mechanism 340, and a navigation control 338. The storage compartment 336 is adapted to store a plurality of lancets, additional cartridges, test sensors and/or other items. It is contemplated that other storage compartments may be used instead of, or in addition to storage compartment 336. Some non-limiting examples of other storage compartments may be storage compartments 60a-c of FIG. 1a.

To prepare the sensor-dispensing instrument 310 for testing, according to one method, the sensor-dispensing instrument 310 is placed in an closed position. The user slides the sensor-advancement mechanism 320 causing one of the plurality of test sensors 318 to advance from the cartridge 316. It is contemplated that the user may activate the sensor-advancement mechanism 320 by other methods such as pressing a button. The sensor-dispensing instrument 310 automatically moves one of the test sensors 318 into the test-sensor receptacle 328 without any manual handling of the test sensor. This is shown in FIG. 4a where a test sensor 318a is located in the test-sensor receptacle 328. It is advantageous for the sensor-advancement mechanism 320 to place the test sensors 318, one at a time, directly into the test-sensor receptacle 328 so as to reduce the requisite amount of user manipulation. The sensor-dispensing instrument 310 may be moved to open position to continue the testing process by moving the cap 312 with respect to the body 314 via the hinge 315.

Alternate Embodiment A

A sensor-dispensing instrument adapted to determine an analyte concentration of a fluid, the instrument comprising:
a body;
a cap being adapted to move between an open position and a closed position, the cap and body being adapted to correspond with each other to form the closed position;
a cartridge containing a plurality of test sensors, the cartridge being located substantially within the cap;
a test-sensor receptacle;

a sensor-advancement mechanism being adapted to advance the plurality of test sensors, one at a time, to a position that allows a user to manually remove the test sensor and place the test sensor in the test-sensor receptacle; and a lancing device including a lancet.

Alternate Embodiment B

The sensor-dispensing instrument of Alternate Embodiment A further including a cocking device adapted to prepare the lancet for firing.

Alternate Embodiment C

The sensor-dispensing instrument of Alternate Embodiment A further including a firing mechanism adapted to fire the lancet.

Alternate Embodiment D

The sensor-dispensing instrument of Alternate Embodiment A wherein the lancing device is adjacent to the test-sensor receptacle.

Alternate Embodiment E

The sensor-dispensing instrument of Alternate Embodiment A wherein the lancing device includes a lancing endcap.

Alternate Embodiment F

The sensor-dispensing instrument of Alternate Embodiment A wherein the body forms a storage compartment adapted to store a plurality of lancets, test sensors or a cartridge.

Alternate Embodiment G

The sensor-dispensing instrument of Alternate Embodiment A wherein the plurality of sensors is electrochemical sensors.

Alternate Embodiment H

The sensor-dispensing instrument of Alternate Embodiment A wherein the plurality of sensors is optical sensors.

Alternate Embodiment I

The sensor-dispensing instrument of Alternate Embodiment A wherein the cap is adapted to be removable from the body.

Alternate Embodiment J

The sensor-dispensing instrument of Alternate Embodiment A wherein the body has a top surface and a bottom surface, the cap being adapted to correspond with the top surface and the bottom surface of the body.

Alternate Embodiment K

The sensor-dispensing instrument of Alternate Embodiment A wherein the cap is connected to the body via a hinge.

Alternate Embodiment L

The sensor-dispensing instrument of Alternate Embodiment A further including a detection mechanism that alerts a user when the cap is not in the closed position.

Alternate Embodiment M

The sensor-dispensing instrument of Alternate Embodiment A wherein the cap in the closed position allows viewing of the plurality of test sensors.

Alternate Embodiment N

The sensor-dispensing instrument of Alternate Embodiment M wherein the cap forms a window.

Alternate Embodiment O

The sensor-dispensing instrument of Alternate Embodiment A wherein the cartridge further includes a calibration information device that contains calibration information about the plurality of test sensors.

Alternate Embodiment P

The sensor-dispensing instrument of Alternate Embodiment A wherein the plurality of test strips is stacked horizontally within the cap.

Alternate Embodiment Q

The sensor-dispensing instrument of Alternate Embodiment A wherein the plurality of test strips is stacked vertically within the cap.

Alternate Embodiment R

The sensor-dispensing instrument of Alternate Embodiment A wherein the cartridge is located entirely within the cap.

Alternate Embodiment S

The sensor-dispensing instrument of Alternate Embodiment A further including an ejection mechanism adapted to eject one of the plurality of test sensors from the test-sensor receptacle.

Alternate Embodiment T

The sensor-dispensing instrument of Alternate Embodiment A wherein the cap includes a flip-lid mechanism.

Alternate Embodiment U

A sensor-dispensing instrument adapted to determine an analyte concentration of a fluid, the instrument comprising:
a body;
a cap being adapted to move between an open position and a closed position, the cap and body being adapted to correspond with each other to form the closed position;
a cartridge containing a plurality of test sensors, the cartridge being located substantially within the cap;
a test-sensor receptacle;
a sensor-advancement mechanism being adapted to advance the plurality of test sensors, one at a time, to a position that allows a user to manually remove the test sensor and place the test sensor in the test-sensor receptacle.

Alternate Embodiment V

The sensor-dispensing instrument of Alternate Embodiment U wherein the plurality of sensors is electrochemical sensors.

Alternate Embodiment W

The sensor-dispensing instrument of Alternate Embodiment U wherein the plurality of sensors is optical sensors.

Alternate Embodiment X

The sensor-dispensing instrument of Alternate Embodiment U wherein the cap is adapted to be removable from the body.

Alternate Embodiment Y

The sensor-dispensing instrument of Alternate Embodiment U wherein the body has a top surface and a bottom surface, the cap being adapted to correspond with the top surface and the bottom surface of the body.

Alternate Embodiment Z

The sensor-dispensing instrument of Alternate Embodiment U wherein the cap is connected to the body via a hinge.

Alternate Embodiment AA

The sensor-dispensing instrument of Alternate Embodiment U further including a detection mechanism that alerts a user when the cap is not in the closed position.

Alternate Embodiment BB

The sensor-dispensing instrument of Alternate Embodiment U wherein the cap in the closed position allows viewing of the plurality of test sensors.

Alternate Embodiment CC

The sensor-dispensing instrument of Alternate Embodiment BB wherein the cap contains a window.

Alternate Embodiment DD

The sensor-dispensing instrument of Alternate Embodiment U wherein the cartridge further includes a calibration information device that contains calibration information about the plurality of test sensors.

Alternate Embodiment EE

The sensor-dispensing instrument of Alternate Embodiment U wherein the plurality of test strips is stacked horizontally within the cap.

Alternate Embodiment FF

The sensor-dispensing instrument of Alternate Embodiment U wherein the plurality of test strips is stacked vertically within the cap.

Alternate Embodiment GG

The sensor-dispensing instrument of Alternate Embodiment U wherein the cartridge is located entirely within the cap.

Alternate Embodiment HH

The sensor-dispensing instrument of Alternate Embodiment U further including an ejection mechanism adapted to eject one of the plurality of test sensors from the test-sensor receptacle.

Alternate Embodiment II

The sensor-dispensing instrument of Alternate Embodiment U wherein the cap includes a flip-lid mechanism.

Alternate Embodiment JJ

A sensor-dispensing instrument adapted to determine an analyte concentration of a fluid, the instrument comprising:
a body;
a cap being adapted to move between an open position and a closed position, the cap and body being adapted to correspond with each other to form the closed position;
a cartridge containing a plurality of test sensors, the cartridge being located substantially within the cap;
a test-sensor receptacle;
a sensor-advancement mechanism being adapted to automatically advance the plurality of test sensors, one at a time, to the test-sensor receptacle; and
a lancing device including a lancet.

Alternate Embodiment KK

The sensor-dispensing instrument of Alternate Embodiment JJ further including a cocking device adapted to prepare the lancet for firing.

Alternate Embodiment LL

The sensor dispensing instrument of Alternate Embodiment JJ further including a firing mechanism adapted to fire the lancet.

Alternate Embodiment MM

The sensor-dispensing instrument of Alternate Embodiment JJ wherein the lancing device is adjacent to the test-sensor receptacle.

Alternate Embodiment NN

The sensor-dispensing instrument of Alternate Embodiment JJ wherein the lancing device includes a lancing endcap.

Alternate Embodiment OO

The sensor-dispensing instrument of Alternate Embodiment JJ wherein the body forms a storage compartment adapted to store a plurality of lancets, test sensors or a cartridge.

Alternate Embodiment PP

The sensor-dispensing instrument of Alternate Embodiment JJ wherein the plurality of test sensors is electrochemical sensors.

Alternate Embodiment QQ

The sensor-dispensing instrument of Alternate Embodiment JJ wherein the plurality of sensors is optical sensors.

Alternate Embodiment RR

The sensor-dispensing instrument of Alternate Embodiment JJ wherein the cap is adapted to be removable from the body.

Alternate Embodiment SS

The sensor-dispensing instrument of Alternate Embodiment JJ wherein the body has a top surface and a bottom surface, the cap being adapted to correspond with the top surface and the bottom surface of the body.

Alternate Embodiment TT

The sensor-dispensing instrument of Alternate Embodiment JJ wherein the cap is connected to the body via a hinge.

Alternate embodiment UU

The sensor-dispensing instrument of Alternate Embodiment JJ wherein the cap in the closed position allows viewing of the plurality of test sensors.

Alternate Embodiment VV

The sensor-dispensing instrument of Alternate Embodiment UU wherein the cap forms a window.

Alternate Embodiment WW

The sensor-dispensing instrument of Alternate Embodiment JJ wherein the cartridge further includes a calibration information device that contains calibration information about the plurality of test sensors.

Alternate Embodiment XX

The sensor-dispensing instrument of Alternate Embodiment JJ wherein the plurality of test strips is stacked vertically within the cap.

Alternate Embodiment YY

The sensor-dispensing instrument of Alternate Embodiment JJ further including an ejection mechanism adapted to eject one of the plurality of test sensors from the test-sensor receptacle.

Alternate Embodiment ZZ

A sensor-dispensing instrument adapted to determine an analyte concentration of a fluid, the instrument comprising:
 a body;
 a cap being adapted to move between an open position and a closed position, the cap and body being adapted to correspond with each other to form the closed position;
 a cartridge containing a plurality of test sensors, the cartridge being located substantially within the cap;
 a test-sensor receptacle; and
 a sensor-advancement mechanism being adapted to automatically advance the plurality of test sensors, one at a time, to the test-sensor receptacle.

Alternate Embodiment AAA

The sensor-dispensing instrument of Alternate Embodiment ZZ wherein the plurality of test sensors is electrochemical sensors.

Alternate Embodiment BBB

The sensor-dispensing instrument of Alternate Embodiment ZZ wherein the plurality of sensors is optical sensors.

Alternate Embodiment CCC

The sensor-dispensing instrument of Alternate Embodiment ZZ wherein the cap is adapted to be removable from the body.

Alternate Embodiment DDD

The sensor-dispensing instrument of Alternate Embodiment ZZ wherein the body has a top surface and a bottom surface, the cap being adapted to correspond with the top surface and the bottom surface of the body.

Alternate Embodiment EEE

The sensor-dispensing instrument of Alternate Embodiment ZZ wherein the cap is connected to the body via hinge.

Alternate Embodiment FFF

The sensor-dispensing instrument of Alternate Embodiment ZZ wherein the cap in the closed position allows viewing of the plurality of test sensors.

Alternate Embodiment GGG

The sensor-dispensing instrument of Alternate Embodiment FFF wherein the cap forms a window.

Alternate Embodiment HHH

The sensor-dispensing instrument of Alternate Embodiment ZZ wherein the cartridge further includes a calibration information device that contains calibration information about the plurality of test sensors.

Alternate Embodiment III

The sensor-dispensing instrument of Alternate Embodiment ZZ wherein the plurality of test strips is stacked vertically in the cap.

Alternate Embodiment JJJ

The sensor-dispensing instrument of Alternate Embodiment ZZ further including an ejection mechanism adapted to eject one of the plurality of test sensors from the test-sensor receptacle.

Alternate Process KKK

A method of using a sensor-dispensing instrument adapted to determine an analyte concentration of fluid, the method comprising the acts of:

providing a sensor-dispensing instrument including a body, a cap, a cartridge, a test-sensor-receptacle, a sensor-advancing mechanism, a lancing device including a lancet, the cap being adapted to move between an open position and a closed position, the cap and body being adapted to correspond with each other to form the closed position, the cartridge containing a plurality of test sensors, the cartridge being located substantially within the cap;

activating the sensor-advancement mechanism such that the plurality of test sensors is advanced one at a time;

manually removing the test sensor and placing the test sensor in the test-sensor receptacle;

generating fluid using the lancet;

placing the fluid on the test sensor; and determining the analyte concentration of the fluid.

Alternate Process LLL

The method of Alternate Process KKK wherein generating the fluid using the lancet includes preparing a cocking device and firing a firing mechanism.

Alternate Process MMM

The method of Alternate Process KKK wherein the cap is adapted to be removable from the body.

Alternate Process NNN

The method of Alternate Process KKK wherein the body has a top surface and a bottom surface, the cap being adapted to correspond with the top surface and the bottom surface of the body.

Alternate Process OOO

The method of Alternate Process KKK wherein the cap is connected to the body via a hinge.

Alternate Process PPP

The method of Alternate Process KKK wherein the sensor-dispensing instrument includes a detection mechanism that alerts a user when the cap is not in the closed position.

Alternate Process QQQ

The method of Alternate Process KKK wherein the plurality of test strips is advanced horizontally from the cap.

Alternate Process RRR

The method of Alternate Process KKK wherein the plurality of test strips is advanced vertically from the cap.

Alternate Process SSS

The method of Alternate Process KKK further including ejecting the test sensor from the test-sensor receptacle via an ejection mechanism.

Alternate Process TTT

The method of Alternate Process KKK wherein the cap includes a flip-lid mechanism.

Alternate Process UUU

A method of using a sensor-dispensing instrument adapted to determine an analyte concentration of fluid, the method comprising the acts of:

providing a sensor-dispensing instrument including a body, a cap, a cartridge, a test-sensor-receptacle, a sensor-advancing mechanism, the cap being adapted to move between an open position and a closed position, the cap and body being adapted to correspond with each other to form the closed position, the cartridge containing a plurality of test sensors, the cartridge being located substantially within the cap;

activating the sensor-advancement mechanism such that the plurality of test sensors is advanced one at a time;

manually removing the test sensor and placing the test sensor in the test-sensor receptacle;

placing the fluid on the test sensor; and determining the analyte concentration of the fluid.

Alternate Process VVV

The method of Alternate Process UUU wherein the body has a top surface and a bottom surface, the cap being adapted to correspond with the top surface and the bottom surface of the body.

Alternate Process WWW

The method of Alternate Process UUU wherein the cap is connected to the body via a hinge.

Alternate Process XXX

The method of Alternate Process UUU wherein the sensor-dispensing instrument includes a detection mechanism that alerts a user when the cap is not in the closed position.

Alternate Process YYY

The method of Alternate Process UUU wherein the plurality of test strips is advanced horizontally from the cap.

Alternate Process ZZZ

The method of Alternate Process UUU wherein the plurality of test strips is advanced vertically from the cap.

Alternate Process AAAA

The method of Alternate Process UUU further including ejecting the test sensor from the test-sensor receptacle via an ejection mechanism.

Alternate Process BBBB

The method of Alternate Process UUU wherein the cap includes a flip-lid mechanism.

Alternate Process CCCC

A method of using a sensor-dispensing instrument adapted to determine an analyte concentration of fluid, the method comprising the acts of:

providing a sensor-dispensing instrument including a body, a cap, a cartridge, a test-sensor-receptacle, a sensor-advancing mechanism, a lancing device including a lancet, the cap being adapted to move between an open position and a closed position, the cap and body being adapted to correspond with each other to form the closed position, the cartridge containing a plurality of test sensors, the cartridge being located substantially within the cap;

activating the sensor-advancement mechanism such that the sensor-advancement mechanism automatically advances the plurality of test sensors, one at a time, to the test-sensor receptacle;
generating fluid using the lancet;
placing the fluid on the test sensor; and
determining the analyte concentration of the fluid.

Alternate Process DDDD

The method of Alternate Process CCCC wherein generating the fluid using the lancet includes preparing a cocking device and firing a firing mechanism.

Alternate Process EEEE

The method of Alternate Process CCCC wherein the cap is adapted to be removable from the body.

Alternate Process FFFF

The method of Alternate Process CCCC wherein the body has a top surface and a bottom surface, the cap being adapted to correspond with the top surface and the bottom surface of the body.

Alternate Process GGGG

The method of Alternate Process CCCC wherein the cap is connected to the body via a hinge.

Alternate Process HHHH

The method of Alternate Process CCCC wherein the sensor-dispensing instrument includes a detection mechanism that alerts a user when the cap is not in the closed position.

Alternate Process IIII

The method of Alternate Process CCCC further including ejecting the test sensor from the test-sensor receptacle via an ejection mechanism.

Alternate Process JJJJ

A method of using a sensor-dispensing instrument adapted to determine an analyte concentration of fluid, the method comprising the acts of:
providing a sensor-dispensing instrument including a body, a cap, a cartridge, a test-sensor-receptacle, a sensor-advancing mechanism, the cap being adapted to move between an open position and a closed position, the cap and body being adapted to correspond with each other to form the closed position, the cartridge containing a plurality of test sensors, the cartridge being located substantially within the cap; and
activating the sensor-advancement mechanism such that the sensor-advancement mechanism automatically advances the plurality of test sensors, one at a time, to the test-sensor receptacle;
placing the fluid on the test sensor; and
determining the analyte concentration of the fluid.

Alternate Process KKKK

The method of Alternate Process JJJJ wherein the body has a top surface and a bottom surface, the cap being adapted to correspond with the top surface and the bottom surface of the body.

Alternate Process LLLL

The method of Alternate Process JJJJ wherein the cap is connected to the body via a hinge.

Alternate Process MMMM

The method of Alternate Process JJJJ wherein the sensor-dispensing instrument includes a detection mechanism that alerts a user when the cap is not in the closed position.

Alternate Process NNNN

The method of Alternate Process JJJJ further including ejecting the test sensor from the test-sensor receptacle via an ejection mechanism.

While the invention has been described with reference to details of the illustrated embodiment, these details are not intended to limit the scope of the invention as defined in the appended claims. For example, the sensor-dispensing instruments may be used for testing fluids other than blood glucose. In fact, the sensor-dispensing instruments may be used in connection with the analysis of any type of chemistry fluid that can be analyzed using reagent material.

The invention claimed is:
1. A sensor-dispensing instrument adapted to determine an analyte concentration of a fluid, the instrument comprising:
a body;
a cap having an open position and a closed position, the cap and the body being adapted to correspond with each other to form the closed position;
a cartridge containing a plurality of test sensors, the cartridge being located entirely within the cap;
a test-sensor receptacle in the body;
a sensor-advancement mechanism in the cap and operatively configured to automatically advance the plurality of test sensors, one at a time, from the cartridge to the test-sensor receptacle; and
a lancing device including a lancet, the lancing device being coupled to the body.
2. The sensor-dispensing instrument of claim 1, wherein the lancing device is adjacent to the test-sensor receptacle.
3. The sensor-dispensing instrument of claim 1, wherein the body forms a storage compartment adapted to store a plurality of lancets, test sensors or a cartridge.
4. The sensor-dispensing instrument of claim 1, wherein the plurality of test sensors is electrochemical sensors.
5. The sensor-dispensing instrument of claim 1, wherein the plurality of sensors is optical sensors.
6. The sensor-dispensing instrument of claim 1, wherein the cap is adapted to be removable from the body.
7. The sensor-dispensing instrument of claim 1, wherein the body has a first surface and a second surface, the test-sensor receptacle being located on the first surface, the cap being adapted to be removably coupled to both the first surface and the second surface of the body.
8. The sensor-dispensing instrument of claim 1, wherein the cap is connected to the body via a hinge.
9. The sensor-dispensing instrument of claim 1, wherein the cap in the closed position allows viewing of the plurality of test sensors.
10. The sensor-dispensing instrument of claim 1, wherein the plurality of test strips is stacked vertically within the cap.
11. The sensor-dispensing instrument of claim 1, further including an ejection mechanism adapted to eject one of the plurality of test sensors from the test-sensor receptacle.

12. A sensor-dispensing instrument adapted to determine an analyte concentration of a fluid, the instrument comprising:
- a body;
- a cap having an open position and a closed position, the cap and the body being adapted to correspond with each other to form the closed position;
- a cartridge containing a plurality of test sensors, the cartridge being coupled to the cap;
- a test-sensor receptacle in the body; and
- a sensor-advancement mechanism in the cap and operatively configured to automatically advance the plurality of test sensors, one at a time, to the test-sensor receptacle.

13. The sensor-dispensing instrument of claim 12, wherein the cartridge is removably coupled to the cap when the cap is in the closed position and in the open position.

14. The sensor-dispensing instrument of claim 12, wherein the plurality of sensors is optical sensors or electrochemical sensors.

15. The sensor-dispensing instrument of claim 12, wherein the cap is adapted to be removable from the body.

16. The sensor-dispensing instrument of claim 12, wherein the body has a first surface and a second surface, the cap being adapted to be removably coupled to both the first surface and the second surface of the body.

17. The sensor-dispensing instrument of claim 12, wherein the cap is connected to the body via hinge.

18. The sensor-dispensing instrument of claim 12, wherein the cap in the closed position allows viewing of the plurality of test sensors.

19. The sensor-dispensing instrument of claim 12, wherein the plurality of test strips is stacked vertically in the cap.

20. The sensor-dispensing instrument of claim 12, further including an ejection mechanism adapted to eject one of the plurality of test sensors from the test-sensor receptacle.

21. A method of using a sensor-dispensing instrument adapted to determine an analyte concentration of fluid, the method comprising the acts of:
- providing a sensor-dispensing instrument including a body, a cap, a cartridge, a test-sensor-receptacle, a sensor-advancing mechanism, a lancing device including a lancet, the cap having an open position and a closed position, the cap and the body being adapted to correspond with each other to form the closed position, the cartridge containing a plurality of test sensors, the cartridge being located entirely within the cap;
- activating the sensor-advancement mechanism such that the sensor-advancement mechanism automatically advances the plurality of test sensors, one at a time, from the cartridge in the cap into the test-sensor receptacle in the body;
- generating fluid using the lancet;
- placing the fluid on the test sensor; and
- determining the analyte concentration of the fluid.

22. The method of claim 21, wherein generating the fluid using the lancet includes preparing a cocking device and firing a firing mechanism.

23. The method of claim 21, wherein the cap is adapted to be removable from the body.

24. The method of claim 21, wherein the body has a top surface and a bottom surface, the cap being adapted to be removably coupled to both the top surface and the bottom surface of the body.

25. The method of claim 21, wherein the cap is connected to the body via a hinge.

26. The method of claim 21, wherein the sensor-dispensing instrument includes a detection mechanism, the detection mechanism determining if the cap is in the open position and in response to the cap being in the open position, the method further comprising alerting a user that the cap is not in the closed position.

27. The method of claim 21, further including ejecting the test sensor from the test-sensor receptacle via an ejection mechanism.

28. A method of using a sensor-dispensing instrument, the method comprising the acts of:
- providing a sensor-dispensing instrument including a body, a cap, a cartridge, a test-sensor-receptacle in the body, and a sensor-advancement mechanism in the cap, the cap having an open position and a closed position, the cartridge containing a plurality of test sensors, the cartridge being removably coupled to the cap in the closed position and in the open position of the cap; and
- activating the sensor-advancement mechanism such that the sensor-advancement mechanism automatically advances the plurality of test sensors, one at a time, from the cartridge into the test-sensor receptacle.

29. The method of claim 28, wherein the body has a top surface and a bottom surface, the cap being adapted to be removably coupled to both the top surface and the bottom surface of the body.

30. The method of claim 28, wherein the cap is connected to the body via a hinge.

31. The method of claim 28, wherein the sensor-dispensing instrument includes a detection mechanism, the method further comprising determining if the cap is not in the closed position, via the detection mechanism, and in response to the cap not being in the closed position, alerting a user that the cap is not in the closed position.

32. The method of claim 28, further including ejecting the test sensor from the test-sensor receptacle via an ejection mechanism.

33. The sensor-dispensing instrument of claim 12, further comprising a detection mechanism, the detection mechanism being configured to determine if the cap is not in the closed position and in response to the cap not being in the closed position, the detection mechanism being configured to alert a user that the cap is not in the closed position.

34. The sensor-dispensing instrument of claim 33, wherein the alert is an audible alert, a visual alert, or both.

35. The sensor-dispensing instrument of claim 12, wherein the sensor-advancement mechanism in the cap is operatively configured to automatically advance the plurality of test sensors, one at a time, from the cartridge to the test-sensor receptacle in the body when the cap is in the closed position.

* * * * *

UNITED STATES PATENT AND TRADEMARK OFFICE
CERTIFICATE OF CORRECTION

PATENT NO. : 7,875,243 B2
APPLICATION NO. : 11/792356
DATED : January 25, 2011
INVENTOR(S) : Benjamin Rush et al.

Page 1 of 2

It is certified that error appears in the above-identified patent and that said Letters Patent is hereby corrected as shown below:

| | | |
|---|---|---|
| Column 17, Line 24 | replace ~~embodiment~~ | with <u>Embodiment</u> |
| Column 19, Line 27 | replace ~~Alt ernate~~ | with <u>Alternate</u> |
| Column 19, Line 34 | replace ~~Alt ernate~~ | with <u>Alternate</u> |
| Column 19, Line 38 | replace ~~Alt ernate~~ | with <u>Alternate</u> |
| Column 19, Line 44 | replace ~~Alt ernate~~ | with <u>Alternate</u> |
| Column 19, Line 48 | replace ~~Alt ernate~~ | with <u>Alternate</u> |
| Column 19, Line 53 | replace ~~Alt ernate~~ | with <u>Alternate</u> |
| Column 19, Line 58 | replace ~~Alt ernate~~ | with <u>Alternate</u> |
| Column 19, Line 63 | replace ~~Alt ernate~~ | with <u>Alternate</u> |
| Column 20, Line 16 | replace ~~Alt ernate~~ | with <u>Alternate</u> |
| Column 20, Line 23 | replace ~~Alt ernate~~ | with <u>Alternate</u> |
| Column 20, Line 28 | replace ~~Alt ernate~~ | with <u>Alternate</u> |
| Column 20, Line 34 | replace ~~Alt ernate~~ | with <u>Alternate</u> |
| Column 20, Line 39 | replace ~~Alt ernate~~ | with <u>Alternate</u> |
| Column 20, Line 44 | replace ~~Alt ernate~~ | with <u>Alternate</u> |
| Column 20, Line 50 | replace ~~Alt ernate~~ | with <u>Alternate</u> |
| Column 20, Line 55 | replace ~~Alt ernate~~ | with <u>Alternate</u> |
| Column 21, Line 9 | replace ~~Alt ernate~~ | with <u>Alternate</u> |
| Column 21, Line 15 | replace ~~Alt ernate~~ | with <u>Alternate</u> |
| Column 21, Line 19 | replace ~~Alt ernate~~ | with <u>Alternate</u> |
| Column 21, Line 27 | replace ~~Alt ernate~~ | with <u>Alternate</u> |
| Column 21, Line 31 | replace ~~Alt ernate~~ | with <u>Alternate</u> |
| Column 21, Line 37 | replace ~~Alt ernate~~ | with <u>Alternate</u> |

Signed and Sealed this
Thirty-first Day of May, 2011

David J. Kappos
*Director of the United States Patent and Trademark Office*

CERTIFICATE OF CORRECTION (continued)
U.S. Pat. No. 7,875,243 B2

Column 21, Line 43    replace ~~Alt ernate~~    with <u>Alternate</u>

Column 21, Line 62    replace ~~Alt ernate~~    with <u>Alternate</u>

Column 22, Line 1    replace ~~Alt ernate~~    with <u>Alternate</u>

Column 22, Line 6    replace ~~Alt ernate~~    with <u>Alternate</u>

Column 22, Line 12    replace ~~Alt ernate~~    with <u>Alternate</u>